United States Patent
Bakus, II et al.

(10) Patent No.: US 11,827,591 B2
(45) Date of Patent: Nov. 28, 2023

(54) COMPOSITIONS AND METHODS OF PREPARATION THEREOF

(71) Applicant: Apeel Technology, Inc., Goleta, CA (US)

(72) Inventors: Ronald C. Bakus, II, Goleta, CA (US); Alena Higgins, Goleta, CA (US); David Fisher, Goleta, CA (US); Charles Frazier, Goleta, CA (US); Louis Perez, Santa Barbara, CA (US); Gabriel Rodriguez, Goleta, CA (US)

(73) Assignee: Apeel Technology, Inc., Goleta, CA (US)

( * ) Notice: Subject to any disclaimer, the term of this patent is extended or adjusted under 35 U.S.C. 154(b) by 0 days.

(21) Appl. No.: 17/515,249

(22) Filed: Oct. 29, 2021

(65) Prior Publication Data

US 2022/0135510 A1 May 5, 2022

Related U.S. Application Data

(60) Provisional application No. 63/108,168, filed on Oct. 30, 2020.

(51) Int. Cl.
  *C07C 51/353* (2006.01)
  *C08J 11/10* (2006.01)
  *C11C 1/02* (2006.01)
  *C08J 11/16* (2006.01)
  *C07D 201/12* (2006.01)

(52) U.S. Cl.
  CPC ........ *C07C 51/353* (2013.01); *C07D 201/12* (2013.01); *C08J 11/10* (2013.01); *C08J 11/16* (2013.01); *C11C 1/02* (2013.01)

(58) Field of Classification Search
  CPC ....... C07C 51/09; C07C 51/353; C97C 63/36; C07D 201/12; C08J 11/10; C08J 11/16
  See application file for complete search history.

(56) References Cited

U.S. PATENT DOCUMENTS

| | | |
|---|---|---|
| 1,016,761 A | 2/1912 | Moore |
| 1,943,468 A | 1/1934 | Bridgeman |
| 2,213,557 A | 9/1940 | Tisdale et al. |
| 2,222,000 A | 11/1940 | Julius |
| 2,223,168 A | 11/1940 | Dombrow et al. |
| 2,275,659 A | 3/1942 | Steinle et al. |
| 2,324,448 A | 7/1943 | Gottlieb |

(Continued)

FOREIGN PATENT DOCUMENTS

| | | |
|---|---|---|
| CA | 2209674 | 8/1996 |
| CN | 86104531 | 2/1988 |

(Continued)

OTHER PUBLICATIONS

Colacino, E. et al., Processing and investigation methods in mechanochemical kinetics, ACS Omega, 3, 9196-9209 (Year: 2018).*

(Continued)

*Primary Examiner* — Yate' K Cutliff

(74) *Attorney, Agent, or Firm* — Fish & Richardson P.C.

(57) ABSTRACT

Described herein are methods of preparing compounds derived from triglycerides or condensation polymers such as polyesters and/or polyamides. The methods may include subjecting triglyceride or condensation polymer containing matter to mechanical processing in the presence of a nucleophile.

13 Claims, 13 Drawing Sheets

(56) References Cited

U.S. PATENT DOCUMENTS

| | | | |
|---|---|---|---|
| 2,333,887 A | 11/1943 | Redlinger | |
| 2,363,232 A | 11/1944 | De Witt | |
| 2,472,794 A | 6/1949 | Cothran | |
| 2,657,282 A | 10/1953 | Winkel | |
| 2,697,793 A | 12/1954 | Trump et al. | |
| 2,840,606 A * | 6/1958 | Miller | C07C 51/06 562/590 |
| 2,857,282 A | 10/1958 | Jansen | |
| 3,189,467 A | 6/1965 | Kalmar | |
| 3,208,951 A | 9/1965 | Berger et al. | |
| 3,232,765 A | 2/1966 | Rosenthal et al. | |
| 3,268,337 A | 8/1966 | Howard et al. | |
| 3,449,108 A | 6/1969 | McConnell et al. | |
| 3,471,303 A | 10/1969 | Hamdy et al. | |
| 3,715,024 A | 2/1973 | Mumma | |
| 3,997,674 A | 12/1976 | Ukai et al. | |
| 4,002,775 A | 1/1977 | Kabara | |
| 4,025,540 A | 5/1977 | Kleemann et al. | |
| 4,115,313 A | 9/1978 | Lyon et al. | |
| 4,421,775 A | 12/1983 | Chan, Jr. | |
| 4,423,071 A | 12/1983 | Chignac et al. | |
| 4,649,057 A | 3/1987 | Thomson | |
| 4,654,370 A | 3/1987 | Marriot et al. | |
| 4,661,359 A | 4/1987 | Seaborne et al. | |
| 4,680,184 A | 7/1987 | Seiden et al. | |
| 4,710,228 A | 12/1987 | Seaborne et al. | |
| 4,726,898 A | 2/1988 | Mills et al. | |
| 4,732,708 A | 3/1988 | Ekman et al. | |
| 4,732,767 A | 3/1988 | Seiden et al. | |
| 4,820,533 A | 4/1989 | Seaborne | |
| 4,857,345 A | 8/1989 | Sardo | |
| 4,874,618 A | 10/1989 | Seaborn | |
| 4,960,600 A | 10/1990 | Kester et al. | |
| 4,962,885 A | 10/1990 | Coffee | |
| 5,019,403 A | 5/1991 | Krochta | |
| 5,051,448 A | 9/1991 | Shashoua | |
| 5,110,509 A | 5/1992 | Peter et al. | |
| 5,126,153 A | 6/1992 | Beck | |
| 2,342,063 A | 2/1994 | Sells | |
| 5,354,573 A | 10/1994 | Gross et al. | |
| 5,366,995 A | 11/1994 | Savage | |
| 5,376,391 A | 12/1994 | Nisperos-Carriedo et al. | |
| 5,389,389 A | 2/1995 | Beck | |
| 5,451,266 A | 9/1995 | Kirk et al. | |
| 5,498,295 A | 3/1996 | Murch et al. | |
| 5,543,164 A | 8/1996 | Krochta et al. | |
| 5,607,970 A | 3/1997 | Ishihara | |
| 5,658,768 A | 8/1997 | Quinlan | |
| 5,741,505 A | 4/1998 | Beyer et al. | |
| 5,827,553 A | 10/1998 | Dimitroglou | |
| 5,832,527 A | 11/1998 | Kawaguchi | |
| 5,906,831 A | 5/1999 | Larsson et al. | |
| 5,925,395 A | 7/1999 | Chen | |
| 5,939,117 A | 8/1999 | Chen et al. | |
| 6,010,726 A | 1/2000 | Evans et al. | |
| 6,033,705 A | 3/2000 | Isaacs | |
| 6,127,561 A | 10/2000 | Jeromin et al. | |
| 6,136,856 A | 10/2000 | Savage et al. | |
| 6,162,475 A | 12/2000 | Hagenmaier et al. | |
| 6,165,529 A | 12/2000 | Yang et al. | |
| 6,241,971 B1 | 6/2001 | Fox et al. | |
| 6,254,645 B1 | 7/2001 | Kellis et al. | |
| 6,255,451 B1 | 7/2001 | Koch et al. | |
| 6,294,186 B1 | 9/2001 | Beerse et al. | |
| 6,348,217 B1 | 2/2002 | Santos et al. | |
| 6,503,492 B2 | 1/2003 | McGlone et al. | |
| 6,723,364 B1 | 4/2004 | Bompeix et al. | |
| 6,783,768 B1 | 8/2004 | Brown et al. | |
| 6,822,105 B1 | 11/2004 | Luxem | |
| 7,373,135 B2 | 5/2008 | Najib-Fruchart et al. | |
| 7,375,135 B2 | 5/2008 | Najib-Fruchart et al. | |
| 7,550,617 B2 | 6/2009 | Imig et al. | |
| 7,708,822 B2 | 5/2010 | Lahav et al. | |
| 7,732,470 B2 | 6/2010 | Imig et al. | |
| 7,754,766 B2 | 7/2010 | Awad | |
| 7,785,897 B2 | 8/2010 | Agnes et al. | |
| 7,851,002 B2 | 12/2010 | Hekal et al. | |
| 7,931,926 B2 | 4/2011 | Lidster et al. | |
| 7,943,336 B2 | 5/2011 | Viksoe-Nielsen et al. | |
| 8,101,221 B2 | 1/2012 | Chen et al. | |
| 8,119,178 B2 | 2/2012 | Lidster et al. | |
| 8,197,870 B2 | 6/2012 | Krasutsky et al. | |
| 8,247,609 B2 | 8/2012 | Roques et al. | |
| 8,263,751 B2 | 9/2012 | Peterson | |
| 8,424,243 B1 | 4/2013 | Narciso et al. | |
| 8,501,445 B2 | 8/2013 | Yoshikawa et al. | |
| 8,546,115 B2 | 10/2013 | Buchert et al. | |
| 8,586,807 B2 | 11/2013 | Hatcher | |
| 8,609,169 B2 | 12/2013 | Chen et al. | |
| 8,752,328 B2 | 6/2014 | Kaiser et al. | |
| 8,846,355 B2 | 9/2014 | Yoshikawa et al. | |
| 9,095,152 B2 | 8/2015 | Munger | |
| 9,102,125 B2 | 8/2015 | Battersby et al. | |
| 9,283,173 B2 | 3/2016 | Lederman | |
| 9,284,432 B2 | 3/2016 | Yoshikawa et al. | |
| 9,475,643 B1 | 10/2016 | Odman et al. | |
| 9,714,399 B2 | 7/2017 | Verkuijl | |
| 9,743,670 B2 | 8/2017 | Grund | |
| 9,743,679 B2 | 8/2017 | Perez et al. | |
| 9,744,542 B2 | 8/2017 | Rogers | |
| 9,770,041 B2 | 9/2017 | Dong et al. | |
| 9,957,215 B2 | 5/2018 | Perez | |
| 10,092,014 B2 | 10/2018 | Holland et al. | |
| 10,150,132 B2 | 12/2018 | Hamamoto et al. | |
| 10,239,069 B2 | 3/2019 | Rogers | |
| 10,266,708 B2 | 4/2019 | Perez | |
| 10,407,377 B2 | 9/2019 | Balms | |
| 10,517,310 B2 | 12/2019 | Perez | |
| 10,537,115 B2 | 1/2020 | Holland et al. | |
| 10,537,130 B2 | 1/2020 | Rogers | |
| 10,561,155 B2 | 2/2020 | Bakus | |
| 2001/0042341 A1 | 11/2001 | Hamersky et al. | |
| 2002/0043577 A1 | 4/2002 | Krasutsky et al. | |
| 2002/0120159 A1 | 8/2002 | Thengumpillil et al. | |
| 2002/0123546 A1 | 9/2002 | Bigg et al. | |
| 2003/0044488 A1 | 3/2003 | Roskam | |
| 2003/0109727 A1 | 6/2003 | Krasutsky et al. | |
| 2003/0124228 A1 | 7/2003 | Goto | |
| 2003/0194445 A1 | 10/2003 | Kuhner et al. | |
| 2004/0022906 A1 | 2/2004 | Petacvich | |
| 2004/0071845 A1 | 4/2004 | Hekal | |
| 2004/0120919 A1 | 6/2004 | Nguyen et al. | |
| 2004/0220283 A1 | 11/2004 | Zhang et al. | |
| 2005/0053593 A1 | 3/2005 | Wang et al. | |
| 2005/0233039 A1 | 10/2005 | Wolfe et al. | |
| 2005/0249856 A1 | 11/2005 | Marangoni | |
| 2006/0037892 A1 | 2/2006 | Blanc | |
| 2006/0057187 A1 | 3/2006 | Eskuchen et al. | |
| 2006/0057259 A1 | 3/2006 | Ripoll et al. | |
| 2006/0153912 A1 | 7/2006 | Habich et al. | |
| 2006/0198924 A1 | 9/2006 | Song et al. | |
| 2006/0292281 A1 | 12/2006 | Kragh et al. | |
| 2007/0116812 A1 | 5/2007 | Msika et al. | |
| 2007/0278103 A1 | 12/2007 | Hoerr et al. | |
| 2008/0026120 A1 | 1/2008 | Petcavich | |
| 2008/0038471 A1 | 2/2008 | Boger et al. | |
| 2008/0119772 A1 | 5/2008 | Coffee | |
| 2008/0254987 A1 | 10/2008 | Liu et al. | |
| 2008/0262190 A1 | 10/2008 | Koskimies et al. | |
| 2008/0269513 A1 | 10/2008 | Sarangan et al. | |
| 2008/0282601 A1 | 11/2008 | Luttke | |
| 2008/0310991 A1 | 12/2008 | Webster et al. | |
| 2009/0035414 A1 | 2/2009 | Cheng et al. | |
| 2009/0041901 A1 | 2/2009 | Elmusa et al. | |
| 2009/0042985 A1 | 2/2009 | Bhaggan et al. | |
| 2009/0104446 A1 | 4/2009 | Guillet et al. | |
| 2009/0123632 A1 | 5/2009 | Klemann et al. | |
| 2009/0142453 A1 | 6/2009 | Lobisser et al. | |
| 2009/0152371 A1 | 6/2009 | Stark et al. | |
| 2009/0163729 A1 | 6/2009 | Li et al. | |
| 2009/0181114 A1 | 7/2009 | Minatelli et al. | |
| 2009/0318579 A1 * | 12/2009 | Ikenaga | C08J 11/24 522/104 |
| 2009/0325240 A1 | 12/2009 | Daniell | |

(56) References Cited

U.S. PATENT DOCUMENTS

| | | |
|---|---|---|
| 2010/0029778 A1 | 2/2010 | Bailey et al. |
| 2010/0104710 A2 | 4/2010 | Petcavich |
| 2010/0186674 A1 | 7/2010 | Cahill, Jr. et al. |
| 2010/0210745 A1 | 8/2010 | McDaniel |
| 2010/0278784 A1 | 11/2010 | Pojasek et al. |
| 2010/0292426 A1 | 11/2010 | Hossainv |
| 2010/0297273 A1 | 11/2010 | Lederman |
| 2010/0310719 A1 | 12/2010 | Finney et al. |
| 2011/0000975 A1 | 1/2011 | Gartstein et al. |
| 2011/0003014 A1 | 1/2011 | Kulikowski |
| 2011/0240064 A1 | 10/2011 | Wales |
| 2011/0244095 A1 | 10/2011 | Sardo |
| 2011/0280942 A1 | 11/2011 | Schad et al. |
| 2011/0319504 A1 | 12/2011 | Koskimies et al. |
| 2012/0003356 A1 | 1/2012 | Ekanayake et al. |
| 2012/0015093 A1 | 1/2012 | Finney et al. |
| 2012/0040076 A1 | 2/2012 | Nichols et al. |
| 2012/0103790 A1 | 5/2012 | Krull et al. |
| 2012/0251675 A1 | 10/2012 | Sowa et al. |
| 2013/0045246 A1 | 2/2013 | Edwards et al. |
| 2013/0095141 A1 | 4/2013 | Schad et al. |
| 2013/0121648 A1 | 5/2013 | Hung et al. |
| 2013/0156970 A1 | 6/2013 | Crawford |
| 2013/0209617 A1 | 8/2013 | Lobisser et al. |
| 2013/0216488 A1 | 8/2013 | Hernandez-Brenes et al. |
| 2013/0266703 A1 | 10/2013 | Hassan et al. |
| 2013/0323378 A1 | 12/2013 | Stark et al. |
| 2014/0033926 A1 | 2/2014 | Passel et al. |
| 2014/0199449 A1 | 7/2014 | Hernandez et al. |
| 2014/0205722 A1 | 7/2014 | Quintanar Guerrero et al. |
| 2014/0221308 A1 | 8/2014 | Baker et al. |
| 2014/0234921 A1 | 8/2014 | Nyyssola et al. |
| 2014/0348945 A1 | 11/2014 | Dong et al. |
| 2014/0357746 A1 | 12/2014 | Ngantung et al. |
| 2015/0021802 A1 | 1/2015 | Wakita |
| 2015/0030780 A1 | 1/2015 | Rogers |
| 2015/0079248 A1 | 3/2015 | Nussinovitch et al. |
| 2015/0210855 A1 | 7/2015 | Firth |
| 2015/0359217 A1 | 12/2015 | Narita et al. |
| 2015/0366230 A1 | 12/2015 | Malefyt et al. |
| 2016/0002483 A1 | 1/2016 | Zhao et al. |
| 2016/0100597 A1 | 4/2016 | Immaraju et al. |
| 2016/0213030 A1 | 7/2016 | Schad |
| 2016/0256429 A1 | 9/2016 | Spanova et al. |
| 2016/0304410 A1 | 10/2016 | Schultz et al. |
| 2016/0324172 A1 | 11/2016 | Williams et al. |
| 2017/0049119 A1 | 2/2017 | Perez et al. |
| 2017/0073532 A1 | 3/2017 | Perez et al. |
| 2017/0251673 A1 | 9/2017 | Cifuentes et al. |
| 2017/0318827 A1 | 11/2017 | Perez et al. |
| 2017/0320077 A1 | 11/2017 | Rogers |
| 2017/0332650 A1 | 11/2017 | Holland |
| 2018/0044276 A1 | 2/2018 | Perez et al. |
| 2018/0092811 A1 | 4/2018 | Klee |
| 2018/0179401 A1 | 6/2018 | Perez et al. |
| 2018/0222835 A1 | 8/2018 | Bakus, II et al. |
| 2018/0258296 A1 | 9/2018 | Perez et al. |
| 2018/0303732 A1 | 10/2018 | Wehner et al. |
| 2018/0317509 A1 | 11/2018 | Van Velzen et al. |
| 2018/0368426 A1 | 12/2018 | Holland et al. |
| 2018/0368427 A1 | 12/2018 | Rogers et al. |
| 2019/0031590 A1 | 1/2019 | Bakus |
| 2019/0104748 A1 | 4/2019 | Kaun et al. |
| 2019/0166901 A1 | 6/2019 | Rogers |
| 2019/0269144 A1 | 9/2019 | Kaun et al. |
| 2019/0269145 A1 | 9/2019 | Bakus, II et al. |
| 2020/0068912 A1 | 3/2020 | Hernandez |
| 2020/0085072 A1 | 3/2020 | Holland et al. |
| 2020/0085092 A1 | 3/2020 | Rogers |
| 2020/0093147 A1 | 3/2020 | Perez |
| 2020/0100514 A1 | 4/2020 | Bakus |
| 2020/0229455 A1 | 7/2020 | Perez |
| 2020/0352184 A1 | 11/2020 | Frazier et al. |
| 2020/0383343 A1 | 12/2020 | Rodriguez et al. |
| 2020/0397012 A1 | 12/2020 | Sandoval et al. |
| 2021/0230095 A1 | 7/2021 | Bakus, II et al. |
| 2021/0253823 A1* | 8/2021 | Eichert ............... B29B 17/0412 |
| 2021/0282432 A1 | 9/2021 | Hernandez et al. |
| 2021/0291074 A1 | 9/2021 | Bakus, II et al. |
| 2021/0337817 A1 | 11/2021 | Lee et al. |
| 2022/0039416 A1 | 2/2022 | Kaun et al. |
| 2022/0046938 A1 | 2/2022 | Perez et al. |
| 2022/0064859 A1 | 3/2022 | Hernandez et al. |
| 2022/0259133 A1 | 8/2022 | Bakus, II et al. |

FOREIGN PATENT DOCUMENTS

| | | |
|---|---|---|
| CN | 1103548 | 6/1995 |
| CN | 1215420 | 4/1999 |
| CN | 1616561 | 5/2005 |
| CN | 1817147 | 8/2006 |
| CN | 1856261 | 11/2006 |
| CN | 1870912 | 11/2006 |
| CN | 101035926 | 9/2007 |
| CN | 101356012 | 1/2009 |
| CN | 101454406 | 6/2009 |
| CN | 101708013 | 5/2010 |
| CN | 102119719 | 7/2011 |
| CN | 102291986 | 12/2011 |
| CN | 102335142 | 2/2012 |
| CN | 102349555 | 2/2012 |
| CN | 103283830 | 9/2013 |
| CN | 103478233 | 1/2014 |
| CN | 103719261 | 4/2014 |
| CN | 103734280 | 4/2014 |
| CN | 104606076 | 5/2015 |
| CN | 104642528 | 5/2015 |
| CN | 105341619 | 2/2016 |
| CN | 105494615 | 4/2016 |
| CN | 106280909 | 1/2017 |
| CN | 107794114 | 3/2018 |
| CN | 107828560 | 3/2018 |
| CN | 110255947 | 9/2019 |
| CN | 112898630 | 6/2021 |
| CN | 113038824 | 6/2021 |
| DE | 2505428 | 8/1976 |
| DE | 3622191 | 1/1988 |
| EP | 0104043 | 3/1984 |
| EP | 0253539 | 1/1988 |
| EP | 0655201 | 5/1995 |
| EP | 1020124 | 7/2000 |
| EP | 1681281 | 7/2006 |
| EP | 2389814 | 11/2011 |
| EP | 2644185 | 10/2013 |
| EP | 2684879 | 1/2014 |
| EP | 3354264 | 8/2018 |
| ES | 1041955 | 8/1999 |
| GB | 421649 | 12/1934 |
| GB | 587532 | 4/1947 |
| GB | 647174 | 12/1950 |
| GB | 2119399 | 11/1983 |
| IN | 192832 | 5/2004 |
| JP | S54-139645 | 10/1979 |
| JP | S58-034034 | 2/1983 |
| JP | S58-89140 | 5/1983 |
| JP | S62-126931 | 6/1987 |
| JP | S63-062574 | 3/1988 |
| JP | H04-016173 | 1/1992 |
| JP | H04-507192 | 12/1992 |
| JP | H06-506166 | 7/1994 |
| JP | H07-075519 | 3/1995 |
| JP | H08-056564 | 3/1996 |
| JP | 2519455 | 7/1996 |
| JP | H10-7892 | 1/1998 |
| JP | H10-298003 | 11/1998 |
| JP | 2002-531075 | 9/2002 |
| JP | 2003-522130 | 7/2003 |
| JP | 2007-502271 | 2/2007 |
| JP | 2007-510014 | 4/2007 |
| JP | 2008-504442 | 2/2008 |
| JP | 2009-527357 | 7/2009 |
| JP | 2010-530795 | 9/2010 |
| JP | 2012-087072 | 5/2012 |
| JP | 2012-515561 | 7/2012 |

(56) References Cited

FOREIGN PATENT DOCUMENTS

| | | |
|---|---|---|
| JP | 2013-139433 | 7/2013 |
| JP | 2014-231481 | 12/2014 |
| JP | 2018-529627 | 10/2018 |
| JP | 2018-534912 | 11/2018 |
| WO | 93/06735 | 4/1993 |
| WO | 2001/001980 | 1/2001 |
| WO | 2004/030455 | 4/2004 |
| WO | 2007/100654 | 9/2007 |
| WO | 2008/142393 | 11/2008 |
| WO | 2009/119730 | 10/2009 |
| WO | 2010/031929 | 3/2010 |
| WO | WO 2010/093320 | 8/2010 |
| WO | 2011/014831 | 2/2011 |
| WO | 2012/042404 | 4/2012 |
| WO | 2012/164561 | 12/2012 |
| WO | 2012/173262 | 12/2012 |
| WO | 2014/162238 | 10/2014 |
| WO | 2014/206911 | 12/2014 |
| WO | 2015/017450 | 2/2015 |
| WO | WO 2015/022519 | 2/2015 |
| WO | 2015/028299 | 3/2015 |
| WO | 2015/052433 | 4/2015 |
| WO | 2015/074144 | 5/2015 |
| WO | 2015/176020 | 11/2015 |
| WO | 2016/168319 | 10/2016 |
| WO | 2016/187581 | 11/2016 |
| WO | WO-2016187581 A1 * 11/2016 ............. A23B 7/154 |
| WO | 2017/043972 | 3/2017 |
| WO | 2017/048951 | 3/2017 |
| WO | 2017/100636 | 6/2017 |
| WO | 2017/132281 | 8/2017 |
| WO | 2017/172951 | 10/2017 |
| WO | 2018/009846 | 1/2018 |
| WO | 2018/042435 | 3/2018 |
| WO | 2018/094269 | 5/2018 |
| WO | 2019/096844 | 5/2019 |
| WO | WO-2020053051 A1 * 3/2020 ............. C08J 11/24 |

OTHER PUBLICATIONS

Kolattukudy, P.E., Cutin form plants, Biopolymers Online, 3a, 40 pages (Year: 2005).*
Matic, M., The chemistry of plant cuticles: a study of cutin form *Agava americana* L., , Biochemical Journal, vol. 63, No. 1, pp. 168-176 (Year: 1956).*
Goje, A.S., et al., Chemical recycling and kinetics of aqueous alkaline depolymerization of Poly(butylene terephthalate) waste, Chem. Eng. Technol. vol. 27, No. 7, pp. 790-799 (Year: 2004).*
Jones et al., "Pulsing with Triton X-100 Improves Hydration and Vase Life of Cut Sunflowers (*Helianthus annuus* L.)," HortScience, 1993, vol. 28, No. 12, p. 1178-1179.
Karabulut, O. et al., "Postharvest ethanol and hot water treatments of table grapes to control gray mold," Postharvest Biology and Technology, 2004, vol. 34, pp. 169-177.
Kebarle, P., "Special Feature: Commentary—A Brief Overview of the Present Status of the Mechanisms Involved in Electrospray Mass Spectrometry," J. Mass Spectrom, 2000, vol. 35, pp. 804-817.
Keller, B., et al., "Review Article: Interferences and Contaminants Encountered in Modern Mass Spectrometry," Analytica Chimica Acta, 2008, vol. 627, pp. 71-81.
Khan et al., "Application of Edible Coating for Improving Meat Quality: A Review," Pakistan Journal of Food Sciences, 2013, 23(2):71-79.
Kolattukudy, P.E., "BiopolyesterMembranes of Plants: Cutin and Suberin," Science, 1980, vol. 208, No. 4447, pp. 990-1000.
Kolattukudy, P.E., "Cutin from plants," Biopolymers Online, 3a, 2005, 40 pages.
Krammer, P., et al., "Hydrolysis of esters in subcritical and supercritical water," Journal of Supercritical Fluids, 2000, vol. 16, pp. 189-206.

Kroll, B., et al., "Review: Chemistry of Secondary Organic Aerosol: Formation and Evolution of Low-volatility Organics in the Atmosphere," Atmospheric Environment, 2008, vol. 42, pp. 3593-3624.
Kubo et al., "Modes of antifungal action of alkanols against *Saccharomyces cerevisiae*," Bioorganic & Medicinal Chemistry, Mar. 2003, 11(6):1117-1122.
Kubo et al., "Structural functions of antimicrobial long-chain alcohols and phenols," Bioorganic & Medicinal Chemistry, Jul. 1995, 3(7):873-880.
Kulkarni et al., "Natural Polymers—A comprehensive review," International Journal of Research in Pharmaceutical and Biomedical Sciences, Dec. 2012, 3(4):1597-1613.
kumitasu.com [online], "About fruit wax and chenpi," Jul. 26, 2015, retrieved on Aug. 16, 2021, retrieved from URL <https://web.archive.org/web/20160409110129/https://www.kumitasu.com/contents/hyoji/806>, 5 pages (with machine translation).
Li, M., et al., "Direct Quantification of Organic Acids in Aerosols by Desorption Electrospray Ionization Mass Spectrometry," Atmospheric Environment, 2009, vol. 43, pp. 2717-2720.
Lin et al., "Innovations in the Development and Application of Edible Coatings for Fresh and Minimally Processed Fruits and Vegetables," Compr. Rev. Food Sci. Food Saf., Jun. 2007, 6(3):60-75.
Loppinet-Serani, A. et al., "Supercritical water for environmental technologies," J Chem Technol Biotechnol, Jan. 12, 2010, vol. 85, pp. 583-589.
Martin, "Preparation of Saturated and Unsaturated Symmetrical Monoglycerides," Journal of American Chemical Society, Jun. 1953, 75(20):5482-5483.
Matic, M., "The chemistry of Plant Cuticles: a study of cutin form *Agave americana* L.," Biochemical Journal, 1956, vol. 63, No. 1, pp. 168-176.
Mattson, F.H., et al., "Synthesis and properties of glycerides," J Lipid Research, Jul. 1962, vol. 3, No. 3, pp. 281-296.
Meihu et al., "Research on Coating of Preserved Egg for Quality-keeping and Fresh-keeping," Wan Fang, Aug. 2007, 17 pages (with English translation).
Morton, H., "The Relationship of Concentration and Germicidal Efficiency of Ethyl Alcohol," Annals New York Academy of Sciences, 53(1), 1950, pp. 191-196.
Mukherjee et al., "Antibacterial activity of long-chain fatty alcohols against mycobacteria," FEMS Microbiol. Lett., Jan. 2013, 338(2):177-183.
Nemoto et al., "Polyols of a cascade type as a water-solubilizing element of carborane derivatives for boron neutron capture therapy," The Journal of Organic Chemistry, Jan. 1992, 57(2):435.
Nizkorodov, S. et al., "Molecular Chemistry of Organic Aerosols through the Application of High Resolution Mass Spectrometry," Phys. Chem. Chem. Phys, 2011, vol. 13, pp. 3612-3629.
Oh, D. et al., "Antimicrobial activity of ethanol, glycerol monolaurate or lactic acid against Listeria monocytogenes," International Journal of Food Microbiology, 1993, vol. 20, pp. 239-246.
Olmez, H. et al., "Potential alternative disinfection methods for organic fresh-cut industry for minimizing water consumption and environmental impact," LWT—Food Science and Technology, 2009, vol. 42, pp. 686-693.
Orts et al., "Edible Films and Coatings: Why, What, and How?," Edible Films and Coatings for Food Applications, 2009, Chapter 1:1-23.
Osman, S. F. et al., "Preparation, Isolation, and Characterization of Cutin Monomers and oligomers from Tomato Peels," J. Agric, Food Chem, 1999, vol. 47, No. 2, pp. 799-802.
PCT International Preliminary Report on Patentability in International Appln. No. PCT/US2016/051936, dated Mar. 29, 2018, 12 pages.
PCT International Preliminary Report on Patentability in International Appln. No. PCT/US2019/049585, dated Mar. 18, 2021, 10 pages.
PCT International Preliminary Report on Patentability in International Appln. No. PCT/US2020/036174, dated Dec. 16, 2021, 9 pages.
PCT International Search Report and Written Opinion for PCT/US2016/051936, dated Jan. 31, 2017, 18 Pages.

(56) References Cited

OTHER PUBLICATIONS

PCT International Search Report and Written Opinion for PCT/US2016/065917, dated Mar. 9, 2017, 10 Pages.
PCT International Search Report and Written Opinion for PCT/US2017/014978, dated Apr. 10, 2017, 13 Pages.
PCT International Search Report and Written Opinion in International Appln. No. PCT/US2019/042693, dated Oct. 2, 2019, 8 pages.
PCT International Search Report and Written Opinion in International Appln. No. PCT/US2019/045784, dated Oct. 22, 2019, 14 pages.
PCT International Search Report and Written Opinion in International Appln. No. PCT/US2019/049585, dated Jan. 13, 2020, 14 pages.
PCT International Search Report and Written Opinion in International Appln. No. PCT/US2020/036174, dated Sep. 7, 2020, 32 pages.
PCT International Search Report and Written Opinion in International Appln. No. PCT/US2021/020692, dated Jun. 1, 2021, 13 pages.
PCT International Search Report and Written Opinion in International Appln. No. PCT/US2021/044535, dated Nov. 17, 2021, 16 pages.
PCT International Search Report and Written Opinion in International Appln. No. PCT/US2021/048301, dated Dec. 7, 2021, 12 pages.
PCT International Search Report and Written Opinion in PCT/US18/46998, dated Dec. 27, 2018, 31 pages.
PCT International Search Report and Written Opinion in PCT/US2014/048707, dated Nov. 13, 2014, 14 pages.
PCT International Search Report and Written Opinion in PCT/US2017/024799, dated Jun. 8, 2017, 13 pages.
PCT International Search Report and Written Opinion in PCT/US2017/041167, dated Oct. 9, 2017, 16 pages.
PCT International Search Report and Written Opinion, PCT Application No. PCT/US16/33617, dated Aug. 26, 2016, 20 Pages.
PCT International Search Report and Written Opinion, PCT Application No. PCT/US17/62399, dated Feb. 16, 2018, 16 Pages.
PCT International Search Report and Written Opinion, PCT Application No. PCT/US2018/46994, dated Dec. 20, 2018, 28 pages.
PCT Invitation to Pay additional Fees and, Where Applicable, Protest Fee in International Appln. No. PCT/US2018/046994, dated Oct. 23, 2018, 2 pages.
Perkins et al., "Ultrasonic fog application of organic acids delays postharvest decay in red bayberry," Postharvest Biology and Technology, Nov. 2017, 13:41-47.
Adkins et al., "Manipulating Avocado Fruit Ripening with 1-Methylcyclopropene," Postharvest Biol. Technol., Jan. 2005, 35(1):33-42.
Alvaro, J. et al., "Effects of peracetic acid disinfectant on the postharvest of some fresh vegetables," Journal of Food Engineering, 2009, vol. 95, pp. 11-15.
Alvira et al., "Pretreatment Technologies for an Efficient Bioethanol Production Process Based on Enzymatic Hydrolysis: A Review," Bio resource Technology, 2010, 101(13):4851-4861.
Andrade, Ricardo D. et al., "Atomizing spray systems for application of edible coatings," Comprehensive Reviews in Food Science and Food Safety, vol. 11, No. 3, 2012, p. 323-337.
Ayala-Zavala, J.F. et al., "High Relative Humidity In-Package of Fresh Cut Fruits and Vegetables: Advantage or Disadvantage Considering Microbiological Problems and Antimicrobial Delivering Systems?," J Food Science, 2008, vol. 73, p. R41-R47.
Baker et al., "Cutin Degradation by Plant Pathogenic Fungi," The American Phytopathological Society, May 15, 1978, 68:1577-1584.
Baldwin et al., "Edible Coatings for Lightly Processed Fruits and Vegetables," HortScience, Feb. 1995, 30(1):35-38.
Banerjee, S. et al., "Review Article: Electrospray Ionization Mass Spectrometry: A Technique to Access the Information Beyond the Molecular Weight of the Analyte," International Journal of Analytical Chemistry, Nov. 2011, vol. 2012, Article ID 282574, 40 pages.

Bateman, A. et al., "The Effect of Solvent on the Analysis of Secondary Organic Aerosol Using Electrospray Ionization Mass Spectrometry," Environ. Sci. Technol., 2008, vol. 42, No. 19, pp. 7341-7346.
Bateman, A., et al, "Supporting Information for Manuscript es-2008-01226w—The Effect of Solvent on the Analysis of Secondary Organic Aerosol Using Electrospray Ionization Mass Spectrometry," [online] 2008; available from the Internet URL: http://aerosol.chem.uci.edu/publications/Irvine/2008.sub.—Bateman.sub.—EST.sub.—SOA.sub.—solvent.sub.—effects.sub.—supporting.sub.—info.pdf, 6 pages.
Bell et al., "The activity of (S)-hydroprene space spray against three stored products pests in a simulated food production environment," Journal of Stored Products Research, Apr. 1999,35(2):117-126.
Ben-Yehoshua, S. et al., "Modified-atmosphere packaging of fruits and vegetables: reducing condensation of water in bell peppers and mangoes," Acta Hort (ISHS), 1998, vol. 464, 387-392.
Berge et al., "Pharmaceutical Salts," J. Pharm. Sci., Jan. 1977, 66(1):1-19.
Bewick, T. et al., "Evaluation of Epicuticular Wax Removal from Whole Leaves with Chloroform," Weed Technology, Jul. 1993, vol. 7, No. 3, pp. 706-716.
Bourtoom, T., "Edible films and coatings: characteristics and properties," International Food Research Journal, 2008, vol. 15, No. 3, pp. 237-248, 13 pages.
Cantwell, M., "Properties and recommended conditions for long-term storage of fresh fruits and vegetables," Nov. 2001, 8 Pages.
Cech, N., et al., "Practical Implications of Some Recent Studies in Electrospray Ionization Fundamentals," Mass Spectrometry Reviews, 2001, vol. 20, pp. 362-387.
Chen, D-R., et al., "Electrospraying of Conducting Liquids for Monodisperse Aerosol Generation in the 4 nm to 1.8 . mu.m Diameter Range," J. Aerosol Sci., 1995, vol. 26, No. 6, pp. 963-977.
Cochran, H.D., "Solvation in supercritical water," Fluid Phase Equilibria, 1992, vol. 71, pp. 1-16.
Dao et al., "Control of Food Spoilage Fungi by Ethanol," Food Control, Mar. 2011, 22(3-4):360-368.
Deell JR et al., "Addition of sorbitol with KMnO4 improves broccoli quality retention in modified atmosphere packages," J Food Oual, 2006, vol. 29, p. 65-75.
Dhall, "Advances in edible coatings for fresh fruits and vegetables: a review," Crit. Rev. Food Sci. Nutr., 2013, 53(5), pp. 435-450.
Duoren et al., "Green Plasticizers," Scientific and Technological Literature Publishing House, the 1st Edition, Oct. 2011, 339-340, 7 pages (with English translation).
Elgimabi and Ahmed, "Effects of Bactericides and Sucrose-Pulsing on Vase Life of Rose Cut Flowers (*Rosa hybirida*)," Botany Research International, 2009, 2(3) p. 164-168.
Enke, C., "A Predictive Model for Matrix and Analyte Effects in Electrospray Ionization of Singly-charged Ionic Analytes," Analytical Chemistry, 1997, vol. 69, No. 23, pp. 4885-4893.
Extended European Search Report for European Patent Application No. EP 14831592.2, dated Mar. 2, 2017, 9 Pages.
Gabler, M., et al., "Impact of Postharvest Hot Water or Ethanol Treatment of Table Grapes on Gray Mold Incidence, Quality, and Ethanol Content," Plant Disease, Mar. 2005, vol. 89, No. 3, pp. 309-316.
Gaskell, S., "Special Feature: Tutorial—Electrospray: Principles and Practice," J. Mass Spectrom, 1997, vol. 32, pp. 677-688.
Gil, M. et al., "Fresh-cut product sanitation and wash water disinfection: Problems and solutions," International Journal of Food Microbiology, 2009, vol. 134, pp. 37-45.
Graca, "Suberin: the biopolyester at the frontier of plants," Frontiers in Chemistry, Oct. 2015, 3(62):1-11.
Graca, J. et al., "Glycerol and glyceryl esters of o-hydroxyacids in cutins," Phytochemistry, 2002, vol. 61, pp. 205-215.
Graca, J. et al., "Linear and branched poly (omega-hydroxyacid) esters in plant cutins," J. Agric. Food Chem., 2010, vol. 58, No. 17, pp. 9666-9674.
Hardenburg, R., et al., "The Commercial Storage of Fruits, Vegetables, and Florist and Nursery Stocks," United States Department of Agriculture, Agriculture Handbook No. 66, Sep. 1986, pp. 6-7, 30, 50-51.

(56) References Cited

OTHER PUBLICATIONS

Hauff, S. et al., "Determination of hydroxylated fatty acids from the biopolymer of tomato cutin and their fate during incubation in soil," Phytochemical Analysis, Aug. 26, 2010, vol. 21, No. 6, pp. 582-589.

He et al., "Stem end blockage in cut Grevillea 'Crimson Yul-lo' inflorescences," Postharvest Biology and Technology, 2006, vol. 41, p. 78-84.

Herrero et al., "Compressed fluids for the extraction of bioactive compounds," TrAC Trends in Analytical Chemistry, 2013, 43(1):67-83.

Hojjati et al., "Chemical Treatments of Eustoma Cut Flower Cultivars for Enhanced Vase Life," Journal of Awiculture and Social Sciences, 2007, vol. 3, No. 3, p. 75-78.

Holcroft, D., "Water Relations in Harvested Fresh Produce," PEF White Paper No. 15-01, The Postharvest Education Foundation (PEF), May 2015, 16 Pages.

Hongyou, "Homemade Fruit and Vegetable Coating Preservative," Vegetables, Nov. 30, 2005, p. 39, 2 pages (with English translation).

Huang et al., "Automation of a Fourier transform ion cyclotron resonance mass spectrometer for acquisition, analysis, and e-mailing of high-resolution exact-mass electrospray ionization mass spectral data," Journal of the American Society for Mass Spectrometry, Nov. 1, 1999, 10(11):1166-1173.

Huang, T-Y., et al., "Electron Transfer Reagent Anion Formation via Electrospray Ionization and Collision-induced Dissociation," Anal Chem., 2006, vol. 78, No. 21, pp. 7387-7391, 9 pages.

Hudson, B., "Fatty Acids," Encyclopedia of Food Sciences and Nutrition (Second Edition), 2003, pp. 2297-2300.

Javad et al., "Effect of Cultivar on Water Relations and Postharvest Quality of Gerbera (*Gerbera jamesonii Bolus* ex.*Hook*f.) Cut Flower," World Applied Sciences Journal, 2012, vol. 18, No. 5, p. 698-703.

Javad et al., "Postharvest evaluation of vase life, stem bending and screening of cultivars of cut gerbera (*Gerberajamesonii Bolux* ex. *Hook*f.) flowers," African Journal of Biotechnology 2011, 10(4), p. 560-566.

Jaworek, A., "Electrospray Droplet Sources for Thin Film Deposition," J. Mater Sci, 2007, vol. 42, pp. 266-297.

Jenkin, S. et al., "Isolation and Compositional Analysis of Plant Cuticle Lipid Polyester Monomers," Journal of Visualized Experiments, 105 e53386, 10 pages, URL: https://www.jove.com/video/53386, 2015.

Jensen et al., "Estimation of the Monoglyceride Content of Milk," Journal of Dairy Science, 1959, 42(2):232-239.

Jerome, F., et al., ""One pot" and selective synthesis of monoglycerides over homogeneous and heterogeneous guanidine catalysts," Green Chem., 2004, vol. 6, pp. 72-74.

Jiabin, "Rubberized fabrics and products thereof," World Rubber Industry, Dec. 2000, 6:27-32, 24 pages (with English translation).

Jingmei et al., "Preparation of modified starch/polylactic acid bleeds," New Chemical Materials, Jun. 2011, 39(6):125-126 and 129 (with English abstract).

Dinani et al., "Optimization of Carboxymethyl Cellulose and Calcium Chloride Dip-Coating on Mushroom Slices Prior to Hot Air Drying Using Response Surface Methodology," Journal of Food Processing and Prevention, Jun. 2014, 38(3):1269-1278.

Rahman et al., "The Effect of a New Coating on the Drying Performance of Fruit and Vegetables Products: Experimental Investigation and Artificial Neural Network Modeling," Foods, Mar. 2020, 9(3), 308, 1-13.

International Search Report and Written Opinion in International Appln. No. PCT/US2021/057448, dated Feb. 18, 2022, 17 pages.

postharvest.ucdavis.edu [online], "Fact Sheets," available on or before Aug. 9, 2016, via Internet Archive: Wayback Machine URL <https://web.archive.org/web/20160809075048/http://postharvest.ucdavis.edu/Commodity_Resources/Fact_Sheets/>, retrieved on Aug. 16, 2021, URL <http://postharvest.ucdavis.edu/Commodity_Resources/Fact_Sheets/>, 3 pages.

Quiros-Sauceda et al., "Edible coatings as encapsulating matrices for bioactive compounds: a review," Journal of Food Science and Technology, Jan. 2014, 51(9), pp. 1674-1685, 12 pages.

Roy, S. et al., "Modified atmosphere and modified humidity packaging of fresh mushrooms," J Food Sci., 1996, vol. 61, p. 391-397.

Rujun et al., "Surface Modification and Physical properties of Inorganic Nanomaterials," University of Technology Press, 1st Edition, Oct. 2009, 43-45, 11 pages (with English translation).

Rutala, W. et al., "Guideline for Disinfection and Sterilization in Healthcare Facilities, 2008," CDC, 2008, 158 Pages.

Sasaki, M. et al., "Cellulose hydrolysis in subcritical and supercritical water," Journal of Supercritical Fluids, 1998, vol. 13, pp. 261-268.

Sasaki, M. et al., "Dissolution and Hydrolysis of Cellulose in Subcritical and Supercritical Water," Ind. Eng. Chem. Res., 2000, vol. 39, pp. 2883-2890.

Savage, P., "Organic Chemical Reactions in Supercritical Water," Chem. Rev., 1999, vol. 99, pp. 603-621.

Schreiber et al., "Transport barriers made of cutin, suberin and associated waxes," Trends in Plant Science, 2010, vol. 15, No. 10, p. 546-553.

Schweizer, P. et al., "Perception of free cutin monomers by plant cells," The Plant Journal, vol. 10, No. 2, 1996, p. 331-341.

Schweizer, P. et al., "Plant Protection by Free Cutin Monomers in Two Cereal Pathosystems," Advances in Molecular Genetics of Plant-Microbe Interactions, 1994, p. 371-374.

Shirazi A, et al., "Controlling relative humidity in modified atmosphere packages of tomato fruit," HortScience, 1992, vol. 27, p. 336-339.

Siekmann et al., "Preparation and structural investigations of colloidal dispersions prepared from cubic monoglyceride-water phases," Int. J. Pharm., Sep. 2002, 244(1-2):33-43.

Spicer et al., "Novel Process for Producing Cubic Liquid Crystalline Nanoparticles (Cubosomes)," Langmuir, Aug. 2001, 17(19):5748-5756.

Steuter et al., "Water Potential of Aqueous Polyethylene Glycol," Plant Physiol., 1981, vol. 67, p. 64-67.

Takats, Z., et al., "Special Feature: Perspective—Ambient Mass Spectrometry Using Desorption Electrospray Ionization (DESI): Instrumentation, Mechanisms and Applications in Forensics, Chemistry, and Biology," J. Mass Spectrom, 2005, vol. 40, pp. 1261-1275.

Tanaka, M., et al., "Quantitative determination of isomeric glycerides, free fatty acids and triglycerides by thin layer chromatography-flame ionization detector system." Lipids, 1980, vol. 15, No. 10, pp. 872-875.

Technical Evaluation Report, "Glycerides (mono and di) Handling/Processing," Compiled by OMRI for the USDA National Organic Program, Jan. 27, 2015, 1-14.

Tegelaar, E.W. et al., "Some mechanisms of flash pyrolysis of naturally occurring higher plant polyesters," Journal of Analytical and Applied Pyrosis, 1989, vol. 15, 2 pages (abstract only).

The Fountainhead Group, Inc., "Burgess Electric Professional Fogger," Manual No. 161128, Revision D, Feb. 25, 2015, retrieved on Jan. 12, 2021, retrieved from URL <https://www.jondon.com/media/pdf/manuals/FG-EGF-EA_manual.pdf>, 8 pages.

TW Search Report in Taiwan Appln. No. 105130215, dated Aug. 6, 2020, 12 pages (with English translation).

United States Environmental Protection Agency, "Containers and Packaging: Product-Specific Data," Nov. 6, 2019, last updated Jan. 28, 2021, retrieved on Oct. 6, 2021, retrieved from URL <https://www.epa.gov/facts-and-figures-about-materials-waste-and-recycling/containers-and-packaging-product-specific-data>, 12 pages.

US Statutory Invention Registration No. H1591, Preparation of Flavor-Enhanced Reduced Calorie Fried Foods, Sep. 3, 1996, 5 pages.

Van Doorn et al., "Alkylethoxylate surfactants for rehydration of roses and Bouvardia flowers," Postharvest Biology and Technology, 2002, vol. 24, p. 327-333.

Van Doorn et al., "Effects of surfactants on the longevity of dry-stored cut flowering stems of rose, Bouvardia, and Astilbe," Postharvest Biology and Technology, 1993, vol. 3, pp. 69-76.

Van Meeteren, "Water Relations and Keeping-Quality of Cut Gerbera Flowers. I. The Cause of Stem Break," Scientia Horticulturae, 1978, vol. 8, p. 65-74.

(56) References Cited

OTHER PUBLICATIONS

Vardar et al., "The application of various disinfectants by fogging for decreasing postharvest diseases of strawberry," Postharvest Biology and Technology, Apr. 2012, 66:30-34.
Vargas et al., "Development of Edible Coatings for Fresh Fruits and Vegetables: Possibilities and Limitations," Fresh Produce, Jan. 2008, 2(2):32-40.
Wang, R. et al., "Evolution of the Solvent Polarity in an Electrospray Plume," J. Am Soc Mass Spectrom, 2010, vol. 21, pp. 378-385.
Watkins, "The Use of 1-Methylcyclopropene (1-MCP) on Fruits and Vegetables," Biotech. Adv., Jul.-Aug. 2006, 24(4):389-409.
Weingartner, H. et al., "Supercritical water as a solvent," Angewandte Chemie, 2005, vol. 44, Issue 18, pp. 2672-2692.
Wikipedia, Anonymous, "Paint-Wikipedia," retrieved from URL <https://en.wikipedia.org/w/index.php?title=Paint&oldid=563291624>, retrieved Jul. 2013, 7 Pages.
Xizhong et al., "Spray drying," the 2nd edition, Chemical Industry Press, Feb. 28, 2003, 147-151, 9 pages.
Yang et al., "Progress on Graft Polymerization of Cellulose," Journal of Cellulose Science and Technology, Sep. 2009, 17(3), 6 pages (with English abstract).
Yeats, T. et al., "The identification of cutin synthase: formation of the plant polyester cutin," Nat Chem Biol., Jul. 2012, vol. 8, No. 7, pp. 609-611, 10 pages.
Zhu, J. et al., "Focus: Electrospray—Formation and Decompositions of Chloride Adduct Ions, [M+Cl], in Negative Ion Electrospray Ionization Mass Spectrometry," J. Am Soc Mass Spectrom, 2000, vol. 11, pp. 932-941.
Zhu, J. et al., "Ranking of a Gas-phase Acidities and Chloride Affinities of Monosaccharides and Linkage Specificity in Collision-induced Decompositions of Negative Ion Electrospray-generated Chloride Adducts of Oligosaccharides," J. Am Soc Mass Spectrom, 2001, vol. 12, pp. 1193-1204.
Chamli et al., "Chemical characterization and thermal properties of kernel oils from Tunisian peach and nectarine varieties of Prunus persica," Grasas Aceites, Jul.-Sep. 2017, 68(3), e211:1-9.
Chetpattananondh et al., "Synthesis of high purity monoglycerides from crude glycerol and palm stearin," Songklanakarin Journal of Science and Technology, Jul. 2008, 30(4):515-521.
Dominguez et al., "An overview on plant cuticle biomechanics," Plant Science, Aug. 2022, 181(2): 77-84.
Dubois et al., "Fatty acid profiles of 80 vegetable oils with regard to their nutritional potential," Eur. J. Lipid Sci. Technol., Jul. 2007, 109(7):710-732.
Franke et al., "Apoplastic polyesters in *Arabidopsis* surface tissues—A typical suberin and a particular cutin," Phytochemistry, Nov. 2005, 66:2643-2658.
Hendrickson et al., "Citrus By-Products of Florida," Agricultural Experiment Stations Bulletin, retrieved from URL <https://ufdc.ufl.edu/UF00027148/00001>, Dec. 1951, 487:5-56.
Hilditch et al., "The Component Fatty Acids and Glycerides of Groundnut Oils," Journal of the Science of Food and Agriculture, Dec. 1950, 1(12):372-379.
Isaacson, "Cutin deficiency in the tomato fruit cuticle consistently affects resistance to microbial infection and biomechanical properties, but not transpirational water loss," The Plant Journal, Oct. 2009, 60(2):363-377.
Liu Yulan, "Modern Processing Technology for Vegetable Oil," Henan Science and Technology Press, Jun. 2015, 260, 2 pages (English translation).
Momeny et al., "Effect of Microwave Pretreatment on the Oil Yield of Mango Seeds for the Synthesis of a Cocoa Butter Substitute," Food Processing and Technology, 2012, 3(7):1-7.
Nawrath, "The Biopolymers Cutin and Suberin," The *Arabidopsis* Book, Apr. 2002, 14 pages.
Neeman et al., "Avocado Oil Production and Chemical Characteristics," JAOCS, Feb. 1987, 64(2):229-232.
Osman et al., "Method for the production and characterization of tomato cutin oligomers," Journal Agricultural and Food Chemistry, 1995, 43(8):2134-2137.
Riederer et al., "Quantitative Gas Chromatographic Analysis of Methyl Esters of Hydroxy Fatty Acids Derived from Plant Cutin," Journal of Chromatography A, 1986, 360:151-161.
Stuchell et al, "Edible Coatings on Frozen King Salmon: Effect of Whey Protein Isolate and Acetylated Monoglycerides on Moisture Loss and Lipid Oxidation", Journal of Food Science, Jan. 1995, 60(1):28-31, 4 pages.
US-Organic.com [online], "100% Pure Certified USDA Organic—Grape Seed Oil," retrieved from URL <https://www.us-organic.com/products/100-pure-certified-usda-organic-grape-seed-oil-2-oz?variant=12643503833187>, retrieved Sep. 29, 2020, 5 pages.
Weber et al., "The Isolation of Monoglycerides from Lard and from Bread," The Journal of the American Oil Chemist Society, Jul. 1952, 261-270.

\* cited by examiner

COMPOSITIONS AND METHODS OF PREPARATION THEREOF

CROSS-REFERENCE TO RELATED APPLICATION

This application claims the benefit of U.S. Patent Application No. 63/108,168, filed on Oct. 30, 2020, which is incorporated herein by reference in its entirety.

TECHNICAL FIELD

The present disclosure relates to compounds and compositions derived from compounds such as condensation polymers or triglycerides and compositions thereof, methods of making said compounds and compositions, and the application of said compounds and compositions in recycling and agricultural coating formulations.

BACKGROUND

Common agricultural products are susceptible to degradation and decomposition (i.e., spoilage) when exposed to the environment. Such agricultural products can include, for example, eggs, fruits, vegetables, produce, seeds, nuts, flowers, and/or whole plants (including their processed and semi-processed forms). Non-agricultural products (e.g., vitamins, candy, etc.) are also vulnerable to degradation when exposed to the ambient environment. The degradation of the agricultural products can occur via abiotic means as a result of evaporative moisture loss from an external surface of the agricultural products to the atmosphere and/or oxidation by oxygen that diffuses into the agricultural products from the environment and/or mechanical damage to the surface and/or light-induced degradation (i.e., photodegradation). Furthermore, biotic stressors such as, for example, bacteria, fungi, viruses, and/or pests can also infest and decompose the agricultural products.

Conventional approaches to preventing degradation, maintaining quality, and increasing the life of agricultural products include refrigeration and/or special packaging. Refrigeration requires capital-intensive equipment, demands constant energy expenditure, can cause damage or quality loss to the product if not carefully controlled, must be actively managed, and its benefits are lost upon interruption of a temperature-controlled supply chain. Special packaging can also require expensive equipment, consume packaging material, increase transportation costs, and require active management. Despite the benefits that can be afforded by refrigeration and special packaging, the handling and transportation of the agricultural products can cause surface abrasion or bruising that is aesthetically displeasing to the consumer and serves as points of ingress for bacteria and fungi. Moreover, the expenses associated with such approaches can add to the cost of the agricultural product.

SUMMARY

This disclosure describes methods for converting polyester- or polyamide-containing compounds into constituent monomers, oligomers, or both; methods of producing cutin-derived monomers, oligomers, or both from plant-matter; and methods of producing constituent monomers, oligomers, or both from triglycerides in seed, bean, nut, kernel, or pulp material of plant matter. These methods generally include mechanochemical processes that decompose or depolymerize the polymeric feedstock to yield the constituent monomers and oligomers.

Although the disclosed inventive concepts include those defined in the attached claims, it should be understood that the inventive concepts can also be defined in accordance with the following embodiments.

In addition to the embodiments of the attached claims and the embodiments described above, the following numbered embodiments are also innovative.

Embodiment 1 is a method for depolymerizing polyester- or polyamide-containing compounds into constituent oligomer and/or monomers, the method comprising:
    contacting a polyester- or polyamide-containing compound with a nucleophile to form a first mixture;
    mechanically processing the first mixture to decompose at least a portion of the polyester- or polyamide-containing compound to yield a second mixture comprising the constituent oligomer and/or monomers of the polyester- or polyamide-containing compound; and
    isolating at least a portion of the constituent oligomer and/or monomers from the second mixture.

Embodiment 2 is the method of embodiment 1, wherein the polyester- or polyamide-containing compound comprises one or more of a condensation polymer and a triglyceride.

Embodiment 3 is the method of embodiment 2, wherein the condensation polymer is selected from cutin, polyethylene terephthalate, polybutylene terephthalate, polytrimethylene terephthalate, polyethylene naphthalate, poly(2-hydroxybutarate), poly(caprolactone), poly(lactic acid), polyhydroxyalkanoates, polyglycolide, polyethylene adipate, polybutylene succinate, nylons, aromatic polyamides, and polyphthalamide.

Embodiment 4 is the method of embodiment 3, wherein the condensation polymer is cutin.

Embodiment 5 is the method of embodiment 2, wherein the polyester-containing compound is a triglyceride.

Embodiment 6 is the method of any one of embodiments 1-5, wherein the nucleophile is selected from a hydroxide, an alkoxide, a carbonate, a metal hydride, and precursors thereof.

Embodiment 7 is the method of embodiment 6, wherein the nucleophile is a hydroxide selected from potassium hydroxide, sodium hydroxide, barium hydroxide, cesium hydroxide, and calcium hydroxide.

Embodiment 8 is the method of any one of embodiments 1-7, wherein a selected amount of the nucleophile is a catalytic amount, a stoichiometric amount, or a superstoichiometric amount.

Embodiment 9 is the method of any one of embodiments 1-8, wherein the first mixture is mechanically processed for about 1 minute to about 24 hours.

Embodiment 10 is the method of any one of embodiments 1-9, wherein the mechanical processing comprises grinding the first mixture.

Embodiment 11 is the method of embodiment 10, wherein grinding the first mixture comprises milling the first mixture.

Embodiment 12 is the method of embodiment 11, wherein the milling is planetary ball milling, and the first mixture is milled at a spinning frequency of about 1 rpm to about 1000 rpm.

Embodiment 13 is the method of any one of embodiments 1-9, wherein the mechanical processing comprises agitating the first mixture.

Embodiment 14 is the method of any one of embodiments 1-13, wherein the mechanical processing reduces the particle size of at least a portion of the second mixture to a mean particle size of less than about 1000 microns.

Embodiment 15 is the method of any one of embodiments 1-14, wherein isolating at least a portion of the constituent monomers from the second mixture comprises subjecting the second mixture to at least one of acidification, distillation, filtration, and centrifugation.

Embodiment 16 is the method of embodiment 15, wherein isolating at least a portion of the constituent monomers comprises treating the second mixture with an acid.

Embodiment 17 is the method of embodiment 16, wherein the acid is an inorganic acid.

Embodiment 18 is the method of embodiment 16 or embodiment 17, wherein the acid is selected from hydrochloric acid, phosphoric acid, and sulfuric acid.

Embodiment 19 is the method of any one of embodiments 16-18, wherein treating the second mixture with an acid forms a solution having a pH less than or equal to 5.

Embodiment 20 is the method of any one of embodiments 16-19, wherein the second mixture is treated with the acid for about 5 minutes to about 24 hours.

Embodiment 21 is the method of any one of embodiments 1-20, wherein the constituent monomers comprise at least one compound of Formula I as described herein.

Embodiment 22 is the method of any one of embodiments 1-20, wherein the constituent monomers comprise at least one compound of Formula II as described herein.

Embodiment 23 is the method of any one of embodiments 1-20, wherein the constituent monomers comprise at least one compound of Formula III as described herein.

Embodiment 24 is method of producing cutin-derived monomers, oligomers, or both from plant-matter, the method comprising:
  obtaining cutin from a cutin-containing portion of plant matter;
  contacting the cutin with a nucleophile to form a first mixture; and
  subjecting the first mixture to mechanical processing to decompose at least a portion of the cutin, thereby yielding a second mixture comprising cutin-derived monomers, oligomers, or both.

Embodiment 25 is the method of embodiment 24, wherein the nucleophile is selected from a hydroxide, an alkoxide, a carbonate, a metal hydride, and precursors thereof.

Embodiment 26 is the method of embodiment 25, wherein the nucleophile is a hydroxide selected from potassium hydroxide, sodium hydroxide, barium hydroxide, cesium hydroxide, and calcium hydroxide.

Embodiment 27 is the method of any one of embodiments 24-26, wherein the cutin is contacted with a catalytic amount, a stoichiometric amount, or a superstoichiometric amount of the nucleophile.

Embodiment 28 is the method of any one of embodiments 24-27, wherein the first mixture is subjected to mechanical processing for about 1 minute to about 24 hours.

Embodiment 29 is the method of any one of embodiments 24-28, wherein the mechanical processing comprises grinding the first mixture.

Embodiment 30 is the method of embodiment 29, wherein grinding the first mixture comprises milling the mixture.

Embodiment 31 is the method of embodiment 30, wherein the milling is planetary ball milling, and the first mixture is milled at a spinning frequency of about 1 rpm to about 1000 rpm.

Embodiment 32 is the method of any one of embodiments 24-31, wherein the second mixture comprises at least one cutin-derived salt of Formula IV as described herein.

Embodiment 33 is the method of any one of embodiments 24-31, wherein the second mixture comprises at least one cutin-derived salt of Formula V as described herein.

Embodiment 34 is the method of any one of embodiments 24-31, wherein the second mixture comprises at least one cutin-derived salt of Formula VI as described herein.

Embodiment 35 is the method of any one of embodiments 24-34, further comprising isolating the cutin-derived monomers from the second mixture, wherein isolating the cutin-derived monomers comprises one or more of acidification, distillation, filtration, and centrifugation.

Embodiment 36 is the method of embodiment 35, wherein the second mixture is acidified.

Embodiment 37 is the method of embodiment 36, wherein the second mixture is acidified with an inorganic acid.

Embodiment 38 is the method of embodiment 37, wherein the inorganic acid is selected from hydrochloric acid, phosphoric acid, and sulfuric acid.

Embodiment 39 is the method of any one of embodiments 37-38, wherein the second mixture is acidified to a pH of less than or equal to 5.

Embodiment 40 is the method of any one of embodiments 35-39, wherein the cutin-derived monomers comprise at least one compound of Formula I as described herein.

Embodiment 41 is the method of any one of embodiments 35-39, wherein the cutin-derived monomers comprise at least one compound of Formula II as described herein.

Embodiment 42 is the method of any one of embodiments 35-39, wherein the cutin-derived monomers comprise at least one compound of Formula III as described herein.

Embodiment 43 is a method of producing constituent monomers from at least a portion of triglycerides of seed, bean, nut, kernel, or pulp material of plant matter comprising:
  obtaining at least partially separated seed, bean, nut, kernel, or pulp material from other portions of plant matter;
  optionally extracting oil from the seed, bean, nut, kernel, or pulp material;
  contacting the separated seed, bean, nut, kernel or pulp material, or the optionally extracted oil therefrom, with a nucleophile to form a first mixture; and
  subjecting the first mixture to mechanical processing to produce a second mixture comprising constituent monomers derived from the triglycerides.

Embodiment 44 is the method of embodiment 43, wherein the nucleophile is selected from a hydroxide, an alkoxide, a carbonate, a metal hydride, and precursors thereof.

Embodiment 45 is the method of embodiment 44, wherein the nucleophile is a hydroxide selected from potassium hydroxide, sodium hydroxide, barium hydroxide, cesium hydroxide, and calcium hydroxide.

Embodiment 46 is the method of any one of embodiments 43-45, wherein the separated seed, bean, nut, kernel or pulp material, or the optionally extracted oil therefrom, is contacted with a catalytic amount, a stoichiometric amount, or a superstoichiometric amount of the nucleophile.

Embodiment 47 is the method of any one of embodiments 43-46, wherein the first mixture is subjected to mechanical processing for about 1 minute to about 24 hours.

Embodiment 48 is the method of any one of embodiments 43-47, wherein to the mechanical processing comprises grinding the first mixture.

Embodiment 49 is the method of embodiment 48, wherein grinding the first mixture comprises milling the mixture.

Embodiment 50 is the method of embodiment 49, wherein the milling is planetary ball milling, and the first mixture is milled at a spinning frequency of about 1 rpm to about 1000 rpm.

Embodiment 51 is the method of any one of embodiments 43-50, wherein the second mixture comprises at least one carboxylate salt or neutral compound of Formula I as described herein.

Embodiment 52 is the method of any one of embodiments 43-50, wherein the second mixture comprises at least one carboxylate salt or neutral compound of Formula II as described herein.

Embodiment 53 is the method of any one of embodiments 43-50, wherein the second mixture comprises at least one carboxylate salt or neutral compound of Formula III as described herein.

Embodiment 54 is the method of any one of embodiments 43-53, further comprising isolating at least a portion of the monomers from the second mixture by one or more of acidification, distillation, filtration and centrifugation.

Embodiment 55 is the method of embodiment 54, wherein the second mixture is acidified.

Embodiment 56 is the method of embodiment 55, wherein the second mixture is acidified with an inorganic acid.

Embodiment 57 is the method of embodiment 56, wherein the organic acid is selected from hydrochloric acid, phosphoric acid, and sulfuric acid.

Embodiment 58 is the method of any one of embodiments 54-57, wherein the second mixture is acidified to a pH of less than or equal to 5.

Embodiment 59 is the method of any one of embodiments 54-58, wherein the monomers comprise at least one compound of Formula I as described herein.

Embodiment 60 is the method of any one of embodiments 54-58, wherein the monomers comprise at least one compound of Formula II as described herein.

Embodiment 61 is the method of any one of embodiments 54-58, wherein the monomers comprise at least one compound of Formula III as described herein.

Mechanochemical reduction of the degree of polymerization provides an efficient option for reducing the degree of polymerization of condensation polymers, and also offers advantages in terms of large-scale production, due at least in part to reduced solvent burden and increased chemical reaction rates. The decomposition products are more easily dissolved that the corresponding polymers and are thus more amenable to down-stream applications. Chemical recycling (e.g., depolymerization of polymers into constituent monomers and using those monomers as starting materials to reconstruct the polymer) can be used advantageously to produce food-safe plastic from waste plastic without the compromised mechanical properties that are often associated with plastics made using physical recycling. Additionally, chemical recycling allows for the removal of organisms or other compounds or contaminants present in the polymer prior to depolymerization.

DETAILED DESCRIPTION

Figure 1:
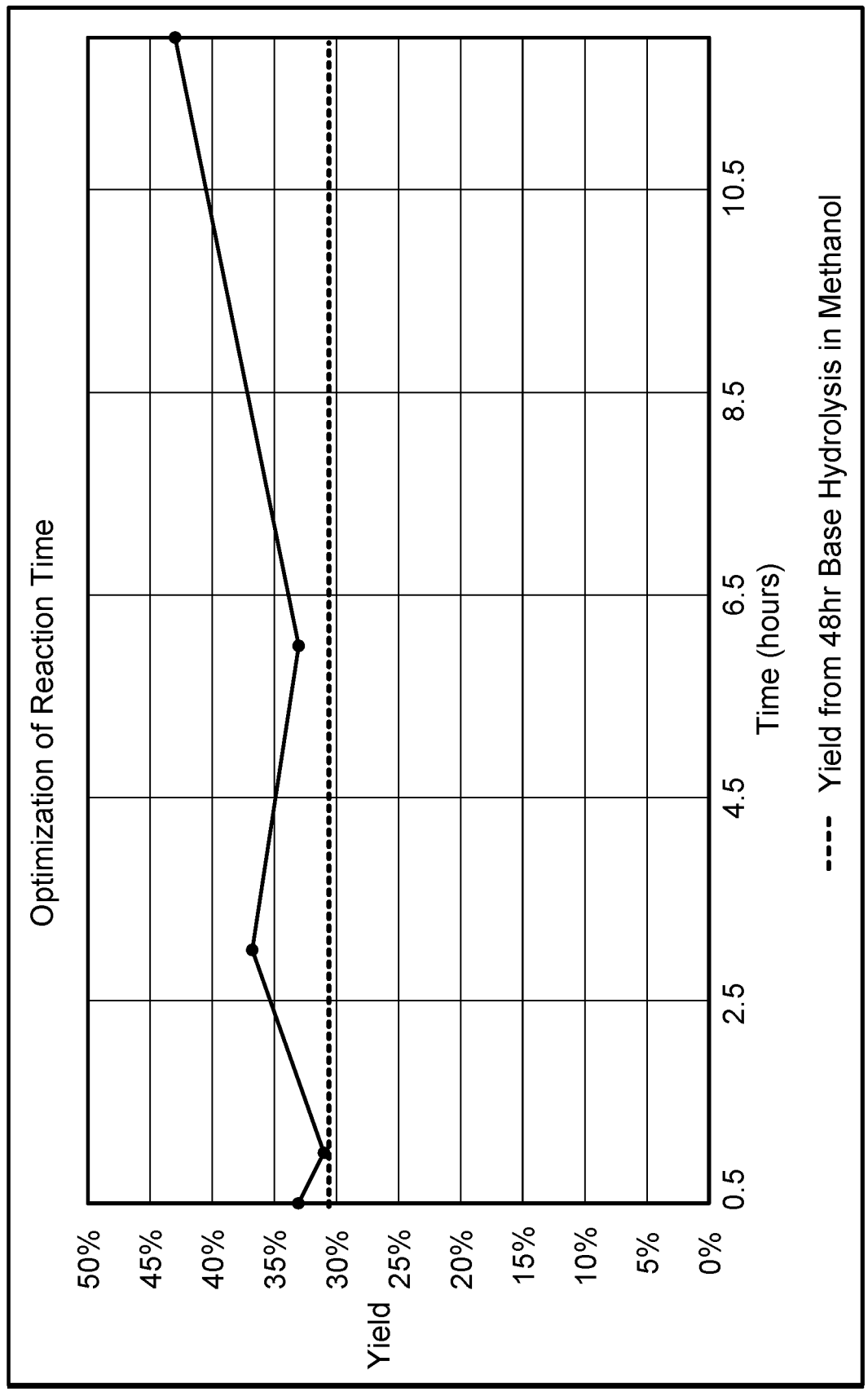
FIG. 1 shows a graph that shows yield as a function of time for the depolymerization of cutin in a ball mill compared to traditional base hydrolysis in methanol.

This disclosure describes mechanochemical processing of feedstock such as condensation polymers (e.g., polyesters, polyamides, cutin, etc.), triglycerides, organic networks, and compounds with hydrolyzable bonds to yield compositions including decomposition or depolymerization products including monomers, oligomers, or both. The mechanochemical processing includes contacting the feedstock with a nucleophile to yield a mixture, and subjecting the mixture to a mechanical process such as grinding (e.g., milling) or agitation (e.g., sonic agitation) to yield the decomposition or depolymerization products. The depolymerization products (e.g., carboxylic acids or their salts) are suitable for variety of applications, including coatings on substrates such as plant matter, produce, and agricultural products.

The present subject matter will now be described more fully with reference to the accompanying figures and examples, in which representative embodiments are shown. The present subject matter may, however, be embodied in different forms and should not be construed as limited to the embodiments set forth herein. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

Definitions

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. Inventive aspects include embodiments in which exactly one member of the group is present in, employed in, or otherwise relevant to a given product or process. Inventive aspects also include embodiments in which more than one, or all of the group members are present in, employed in, or otherwise relevant to a given product or process.

Furthermore, inventive aspects encompass all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where aspects of the invention is/are referred to as comprising particular elements and/or features, certain aspects of the invention consist, or consist essentially of, such elements and/or features. For purposes of simplicity, those embodiments have not been specifically set forth in haec verba herein. It is also noted that the terms "comprising" and "containing" are intended to be open and permit the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

"About" is understood to mean±10% of a particular value.

The term "alkyl", by itself or as part of another substituent, means, unless otherwise stated, a straight or branched chain, or cyclic hydrocarbon radical, or combination thereof, which may be fully saturated or mono- or polyunsaturated, and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl such as "heteroalkyl." Alkyl groups that are limited to hydrocarbon groups are termed "homoalkyl". Unless otherwise specified, each instance of an alkyl group is independently optionally substituted, i.e., unsubstituted (an "unsubstituted alkyl") or substituted (a "substituted alkyl") with one or more substituents, e.g., 1 to 5 substituents, 1 to 3 substituents, or 1 substituent. In certain embodiments, the alkyl group is unsubstituted $C_1$-$C_{10}$ alkyl (e.g., —$CH_3$). In certain embodiments, the alkyl group is substituted $C_1$-$C_{10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkenyl" refers to a radical of a straight-chain or branched hydrocarbon group having 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_2$-$C_{20}$ alkenyl"). In certain embodiments, alkenyl does not contain any triple bonds. In some embodiments, an alkenyl group has 2 to 10 carbon atoms ("$C_2$-$C_{10}$ alkenyl"). In some embodiments, an alkenyl group has 2 to 9, 2 to 8, 2 to 7, 2 to 6, 2 to 5, 2 to 4, 2 to 3, or 2 carbon atoms. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-$C_4$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents, e.g., 1 to 5 substituents, 1 to 3 substituents, or 1 substituent. In certain embodiments, the alkenyl group is unsubstituted $C_2$-$C_{10}$ alkenyl. In certain embodiments, the alkenyl group is substituted $C_2$-$C_{10}$ alkenyl.

"Alkynyl" refers to a radical of a straight-chain or branched hydrocarbon group having 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_2$-$C_{20}$ alkynyl"). In certain embodiments, alkynyl does not contain any double bonds. In some embodiments, an alkynyl group has 2 to 10 carbon atoms ("$C_2$-$C_{10}$ alkynyl"). In some embodiments, an alkynyl group has 2 to 9, 2 to 8, 2 to 7, 2 to 6, 2 to 5, 2 to 4, 2 to 3, or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$-$C_6$ alkenyl groups include the aforementioned $C_2$-$C_4$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents, e.g., 1 to 5 substituents, 1 to 3 substituents, or 1 substituent. In certain embodiments, the alkynyl group is unsubstituted $C_2$-$C_{10}$ alkynyl. In certain embodiments, the alkynyl group is substituted $C_2$-$C_{10}$ alkynyl.

The term "aryl" means, unless otherwise stated, a polyunsaturated, aromatic, hydrocarbon substituent that can be a single ring or multiple rings (preferably 1 to 3 rings), which are fused together or linked covalently. In some embodiments, an aryl group has 6 to 10 carbon atoms (i.e., "$C_6$-$C_{10}$ aryl"). The term "heteroaryl" refers to aryl groups (or rings) that contain one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "cycloalkyl" includes saturated cyclic, bicyclic, tricyclic, or polycyclic hydrocarbon groups having 3 to 12 carbons (i.e., $C_3$-$C_{12}$ cycloalkyl). In some embodiments, the cycloalkyl is a cycloalkyl having 3 to 7 carbon atoms (i.e., $C_3$-$C_7$ cycloalkyl). Any ring atom can be substituted (e.g., by one or more substituents).

The term "polymer" refers to a molecule of high relative molecular mass, the structure of which essentially comprises repeating units derived from molecules of low relative molecular mass.

Unless otherwise indicated, the term "monomer" refers to a molecule which can undergo polymerization, thereby contributing constituent units to the essential structure of a polymer.

The term "oligomer" refers to a molecule of intermediate relative molecular mass, the structure of which essentially comprises a small plurality of units derived from molecules of lower relative molecular mass.

The term "condensation polymer" refers to a polymer composed of at least one type of monomer having not less than two condensable functional groups, the monomers being bound via the binding of the functional groups. If the monomers are difunctional, the condensation product is a linear polymer, and if at least one of the monomers is tri- or tetra-functional, the resulting polymer is a crosslinked polymer. Examples of condensation polymers include polyesters, polyamides, and polycarbonates.

The terms "depolymerizing" and "depolymerization" each refer to a process that reduces the degree of polymerization of a polymer to yield compounds of lower molecular weight (e.g., monomers, oligomers, or both). In some embodiments, the depolymerization is a partial depolymerization that includes degrading a polymer into both constituent monomers and oligomers. In some embodiments, the depolymerization is a total depolymerization that comprises completely degrading a polymer into constituent monomers.

The terms "decompose," "decomposing," or "decomposition" refer to a process that converts a compound (e.g., subjected to a mechanochemical process) into constituent units (e.g., constituent monomers). Decomposition can include depolymerization process (e.g., depolymerization of cutin). Decomposition products include constituent monomers, oligomers, or both.

The term "constituent monomer" refers to a compound that is derived from the decomposition of a compound (e.g., subjected to a mechanochemical process). For purposes of this disclosure, a constituent monomer can be a charged chemical species (e.g., a fatty acid carboxylate) or a neutral chemical species obtained by treatment of a charged chemical species (e.g., a fatty acid obtained by acidification of a fatty acid carboxylate). A constituent monomer is the monomer of a polymer a compound derived from a triglyceride.

"Polyester-containing compound" refers to a compound comprising more than one ester group as part of its chemical composition. A polyester-containing compound can be a condensation polymer with repeating units linked by esters (e.g., a condensation polymer such as a polyester) or a compound in which the ester groups are chemically linked to the compound, but do not form a repeating structure (e.g., a triglyceride).

"Polyamide-containing compound" refers to a compound comprising more than one amide group as part of its chemical composition. A polyamide-containing compound may be a condensation polymer with repeating units linked by the amides.

"Substantially decomposed" means that a compound is 70% to 100% decomposed into constituent units (e.g., constituent monomers).

"Substantially depolymerized" means 70% to 100% depolymerized into constituent monomers, oligomers, or both.

Compounds, Compositions, and Methods of their Preparation

This disclosure describes compounds and compositions derived from sources such as plant matter and methods of their preparation. The compositions can be formed by decomposition (e.g., depolymerization) of a polymer (e.g., a condensation polymer including cutin or other polyesters or a triglyceride), and include hydroxy fatty acids and hydroxy fatty esters (as well as their oligomers and mixtures thereof) found in the cuticle layer or other polymer network. The resulting compositions can subsequently be applied to other plant or agricultural products to form a protective coating over the products, or to enhance or modify existing coatings (either naturally occurring or deposited coatings) that are on an outer surface of the products. The applied coatings may, for example, serve to protect the products from biotic stressors such as bacteria, fungi, viruses, or pests. The applied coatings can serve to increase the shelf life of produce without refrigeration, to control the rate of ripening of produce, or both. In the case of plant matter, the methods of forming the compositions can result in the compositions being substantially free of other plant-derived compounds (e.g., proteins, polysaccharides, phenols, lignans, aromatic acids, terpenoids, flavonoids, carotenoids, alkaloids, alcohols, alkanes, and aldehydes), thereby improving the efficacy of protective coatings formed from the compositions.

Methods of recycling compounds such as condensation polymers including polyester- or polyamide-containing compounds are also described. Chemical recycling can include depolymerizing polymers into their constituent monomers and using those monomers as starting materials to reconstruct the polymer. This type of recycling can be used to produce food-safe plastic from waste plastic that does not have the compromised mechanical properties that are often associated with plastics made using physical recycling. Additionally, chemical recycling allows for the removal of organisms or other compounds or contaminants present in the polymer prior to depolymerization. Methods of chemical recycling include contacting condensation polymer-containing materials with a nucleophile (e.g., a strong base) to yield a mixture, and mechanically processing the mixture to depolymerize the condensation polymer into a composition comprising constituent monomers, oligomers, or both. Mechanical depolymerization allows for rapid, effective, and scalable depolymerization.

Some embodiments include converting polyesters into decomposition products (constituent monomers, oligomers, or both) by contacting a polyester-containing compound with a nucleophile to form a first mixture and subjecting the first mixture to mechanical processing, thereby decomposing at least a portion of the polyester-containing compound in the first mixture to yield a second mixture including decomposition products of the polyester-containing compound. At least a portion of the decomposition products can be isolated from the second mixture. The polyester-containing compounds can include triglycerides and condensation polymers (e.g., polyesters). The triglyceride can be obtained commercially or extracted from a seed, bean, nut, kernel, or pulp material of plant matter.

Converting polyamides into decomposition products is also described. These methods include contacting a polyamide-containing compound with a nucleophile to yield a first mixture, and subjecting the first mixture to mechanical processing to decompose at least a portion of the polyamide-containing compound to yield a second mixture that contains decomposition products of the polyamide-containing compound. At least a portion of the decomposition products can be isolated from the second mixture.

Starting Compositions

Triglycerides

The polyester-containing compound can be a triglyceride. The triglyceride can be commercially available or extracted from the seed, bean, nut, kernel, or pulp material of plant-matter. Oil-comprising triglycerides can be extracted from plant matter. For example, the triglycerides can be extracted by mechanically pressing the plant matter (e.g., hydraulic pressing, screw pressing), by using organic solvents (e.g., hexanes, heptane, ethyl acetate, ethanol, methanol, diethyl ether, toluene), by using supercritical solvents (e.g., $CO_2$, propane), by distillation (steam, water, solvent), by maceration, or by the enfleurage method. The triglycerides can be extracted from seeds including rapeseed, grapeseed, citrus seed, apple seed, sunflower seed, cottonseed, mango seed, safflower seed, and pumpkin seed. As another example, the triglycerides can be extracted from beans such as soy, cacao, castor, and coffee beans. Optionally, the triglycerides can be extracted from nuts such as peanuts, shea nuts, and tree nuts, or from kernels such as cherry kernels, stone fruit kernels, palm kernels, and avocado pits. In some cases, the triglycerides are extracted from pulp material such as, for example, coconut, olive, palm, corn, or wood pulp.

In some embodiments, the triglyceride comprises the reaction product of glycerol and three fatty acids. In some embodiments, the fatty acids are each independently saturated or unsaturated, and have a carbon chain length of at least 7 carbon atoms (e.g., 7 to 21, or 16 to 18 carbon atoms). In some embodiments, the triglyceride comprises the reaction product of glycerol and three occurrences of a compound of Formula I, the reaction product of glycerol and three occurrences of a compound of Formula II, or the reaction product of glycerol and three occurrences of a compound of Formula III. In some embodiments, the triglyceride comprises the reaction product of glycerol and three compounds independently selected from compounds of Formula I, Formula II, and Formula III.

In some embodiments, the triglyceride comprises the reaction product of glycerol and one occurrence of the compound of Formula I and two occurrences of the compound of Formula II, the reaction product of glycerol and one occurrence of the compound of Formula II and two occurrences of the compound of Formula I, the reaction product of glycerol and one occurrence of the compound of Formula I and two occurrences of the compound of Formula III, the reaction product of glycerol and one occurrence of the compound of Formula III and two occurrences of the compound of Formula I, the reaction product of glycerol and one occurrence of the compound of Formula II and two occurrences of the compound of Formula III, the reaction product of glycerol and one occurrence of the compound of Formula III and two occurrences of the compound of Formula II, or the reaction product of glycerol, one occurrence of the compound of Formula I, one occurrence of the compound of Formula II, and one occurrence of the compound of Formula III.

Condensation Polymers

Condensation polymers that can be subjected to the disclosed methods include polyesters (e.g., natural or synthetic polyesters) and polyamides (e.g., natural or synthetic polyamides).

Examples of Polyesters and Polyamides

Exemplary polyesters and polyamides that can be treated by the disclosed methods include cutin, polyethylene terephthalate, poly(2-hydroxybutarate), poly(caprolactone), poly(lactic acid), polyhydroxyalkanoates, nylons, aromatic polyamides, and polyphthalamides. Other dimers, trimers, and oligomer analogs of the polyester- and polyamide-containing compounds can also be treated by the disclosed methods.

Cutin

In some embodiments, cutin is derived from plant skins. Embodiments include separating (or at least partially separating) cutin-containing portions of plant matter from non-cutin-containing portions, and obtaining cutin from the cutin-containing portions. In one example in which the cutin-containing portion is a fruit peel, the peel is separated from the fruit body, and/or the cutin is separated from the peel.

To form a cutin-derived composition (e.g., a cutin-derived plant extract composition), cutin-containing portions of plant matter can be separated (e.g., at least partially separated) from non-cutin-containing portions. Separation can be achieved by a number of methods, either alone or in combination with one another.

The cutin can be derived from plant matter. Plant matter typically includes some portions that contain cutin and/or have a high density of cutin (e.g., fruit peels, leaves, shoots, etc.), as well as other portions that do not contain cutin or have a low density of cutin (e.g., fruit flesh, seeds, etc.). The cutin-containing portions can be used to produce compositions comprising cutin-derived monomers and/or oligomers, and can also include other constituents such as proteins, polysaccharides, phenols, lignans, aromatic acids, terpenoids, flavonoids, carotenoids, alkaloids, alcohols, alkanes, and aldehydes. The low cutin density or non-cutin-containing portions can lack the decomposition products, or otherwise include a much lower ratio of monomer and/or oligomer units to the other constituents as compared to the higher density cutin-containing portions.

Cutin comprises polymers of hydroxy fatty acids. Typical constituent monomers that make up the cutin polymers include, e.g., 16-hydroxyhexadecanoic acid, 9,16-dihydroxyhexadecanoic acid, 10,16-dihydroxyhexadecanoic acid, 18-hydroxyoctadecanoic acid, 18-hydroxy-(9Z)-octadec-9-enoic acid, 9,10-epoxy-18-hydroxyoctadecanoic acid, 9,10,18-trihydroxyoctadecanoic acid, or a combination thereof. The exact products that result directly from mechanochemical decomposition depend, at least in part, on the particular plant source of the cutin and the conditions for mechanochemical decomposition. For example, cutin from tomatoes tends to have a high proportion of $C_{16}$ fatty acids (e.g., fatty acids having a carbon chain length of 16), such as that of FIGS. 5A, 5C, and 5E, whereas cutin from cranberries tends to have a high proportion of $C_{18}$ fatty acids, such as that of FIGS. 5B, 5D, and 5F.

Cutin-derived monomers include palmitic acid-derived monomers such as 16-hydroxyhexadecanoic acid, 7,16-dihydroxyhexadecanoic acid, 8,16-dihydroxyhexadecanoic acid, 9,16-dihydroxyhexadecanoic acid, and 10,16-dihydroxyhexadecanoic acid; palmitoleic acid-derived monomers such as (Z)-16-hydroxyhexadec-9-enoic acid, 9,10-epoxy-16-hydroxyhexadecanoic acid, and 9,10,16-trihydroxyhexadecanoic acid; steric acid-derived monomers such as 18-hydroxyoctadecanoic acid, 9,18-dihydroxyoctadecanoic acid, and 10,18-dihydroxyoctadecanoic acid; oleic acid-derived monomers such as (Z)-18-hydroxyoctadec-9-enoic acid, 9,10-epoxy-18-hydroxyoctadecanoic acid, 9,10,18-trihydroxyoctadecanoic acid, and (Z)-octadec-9-enedioic acid; and linoleic acid-derived monomers such as (9Z,12Z)-18-hydroxyoctadeca-9,12-dienoic acid, (Z)-9,10-epoxy-18-hydroxyoctadec-12-enoic acid, (Z)-9,10,18-trihydroxyoctadec-12-enoic acid, and (6Z,9Z)-octadeca-6,9-dienedioic acid.

Other Compounds

In some embodiments, compounds subjected to the disclosed methods include a single ester group. The compounds can be dimers, trimers, oligomers, or fragments thereof. For instance, the compound may have one of the following structures:

Hydroxides and Treatment Options

In some cases, the nucleophile is a hydroxide (e.g., a Group I or Group II metal hydroxide, such as lithium hydroxide, potassium hydroxide, sodium hydroxide, barium hydroxide, magnesium hydroxide, cesium hydroxide, or calcium hydroxide). In certain cases, the nucleophile is a precursor or compound that generates hydroxide in a suitable reaction medium (e.g., ammonia in water). The nucleophile, temperature, reaction time, and/or spinning frequency can be adjusted such that a condensation polymer or triglyceride is substantially decomposed (e.g., depolymerized or hydrolyzed) by the nucleophile into a plurality of condensation polymer- or triglyceride-derived decomposition products (e.g., cutin-derived monomers or oligomers, monoacylglycerides, salts of fatty acids, terephthalic acid, etc.). The concentration of metal hydroxide, presence or absence

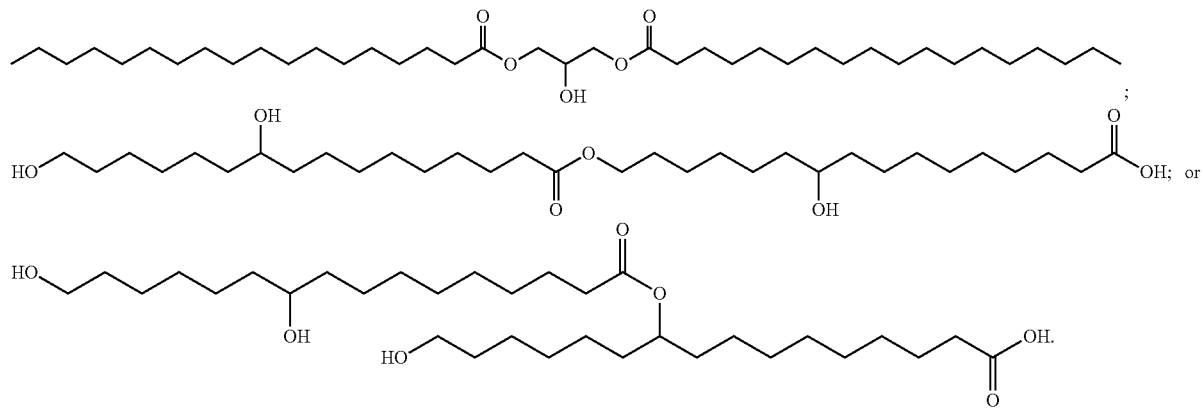

Nucleophile Treatment

The disclosed methods include contacting a compound, such as a polyester- or polyamide containing compound, with a nucleophile. In some cases, the nucleophile includes hydroxides, metal hydrides, and precursors thereof (e.g., carbonates). In some cases, the nucleophile is selected from a hydroxide base, an alkoxide base, a carbonate base, and a hydride base. A polymer such as a polyester-containing compound can be treated with a nucleophile for a certain length of time (e.g., about 1 minute to about 24 hours).

Ranges of Amount of Nucleophile

The nucleophile can be present in a catalytic amount (e.g., less than 1 equiv. (w/w) of the nucleophile to the polyester- or polyamide-containing compound), a stoichiometric amount (e.g., about 1 equiv. (w/w) of the nucleophile to the polyester- or polyamide-containing compound), or a superstoichiometric amount (e.g., greater than 1 equiv. (w/w) of the nucleophile to the polyester- or polyamide-containing compound). In some embodiments the nucleophile loading is 0.0001 to 0.001, 0.001 to 0.01, 0.01 to 1, 0.03 to 10, 1 to 3.0, 3 to 10, 10 to 20, 10 to 30, 10 to 100, or 0.5 to 5 equiv. (w/w). The nucleophile loading is typically sufficient to substantially decompose the polyester- or polyamide-containing compound.

The amount of nucleophile to be used depends, at least in part, on the extent to which a polyester- or polyamide-containing compound is to be decomposed into decomposition products. An amount of nucleophile sufficient to partially or fully decompose the compound into constituent monomers (e.g., a triglyceride decomposing into constituent monomers) can be used.

of solvent, pH of the solution, and/or thermodynamic sink can facilitate the preservation of the depolymerized condensation polymer or decomposed triglyceride constituents (i.e., monomeric and/or oligomeric forms such as cutin monomers, monoacylglycerides, salts of fatty acids, terephthalic acid, lactams, etc.), such that oligomerization or repolymerization of the liberated constituents (e.g., monomers and/or oligomers) is reduced or prevented.

Decomposition can include saponifying a polyester- or polyamide-containing compound. Depolymerizing can occur in the presence of a solvent. In some cases, the solvent is water, an alcohol (e.g., methanol or ethanol), or a mixture thereof. In some cases, the amount of solvent used is not sufficient to dissolve the components of the mixture to which it is added (e.g., the solvent results in a slurry). In other embodiments, depolymerizing occurs in a solvent-free environment.

In some embodiments, decomposition includes direct halogenation (e.g., chlorination, bromination, or iodination) of condensation polymers (e.g., cutin into halogenated monomers, oligomers, or combinations thereof).

In some embodiments, decomposition includes direct reduction of condensation polymers (e.g., ester or carbonyl to alcohol containing monomers, oligomers, or combinations thereof).

Treatment Time (Nucleophile)

A mixture comprising a compound described herein (e.g., a polyester-containing compound) is typically subjected to a nucleophile treatment for a length of time between 1 minute and 24 hours (e.g., at least 5, 10, 30, or 60 minutes). In some embodiments, the length of time is 1 to 5, 1 to 10, 1 to 24, or 1 to 48 hours. The length of time can be tuned to result in different concentrations of oligomers and monomers in the resulting compositions. For example, longer treatment times will result in a greater degree of depolymerization, yielding a greater concentration of monomers than oligomers in the resulting composition. The length of time can be sufficient to substantially decompose the compound into constituent monomers.

Mechanochemical Processes

A mechanochemical process can be used to at least partially decompose cutin or a fruit peel containing cutin to yield a mixture including a plurality of cutin-derived monomers, oligomers, or combinations thereof. The mechanochemical process causes most of or substantially all of the resulting constituent monomers and/or oligomers of the mixture (e.g., at least 95%) to be initially isolated as charged species (e.g., a base addition salt such as a carboxylate). Isolating the resulting monomers and/or oligomers of the mixture may require additional processes (e.g., acidification).

In some embodiments, the charged species is a salt of a compound of Formula I:

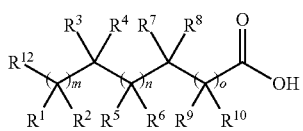

(Formula I)

wherein:

$R^1$, $R^2$, $R^3$, $R^4$, $R^5$, $R^6$, $R^7$, $R^8$, $R^9$, and $R^{10}$ are each independently —H, —OR$^{13}$, —NR$^{13}$R$^{14}$, —SR$^{13}$, halogen, —C$_1$-C$_6$ alkyl, —C$_2$-C$_6$ alkenyl, —C$_2$-C$_6$ alkynyl, —C$_3$-C$_7$ cycloalkyl, aryl, or 5- to 10-membered ring heteroaryl, wherein each alkyl, alkenyl, alkynyl, cycloalkyl, aryl, or heteroaryl is optionally substituted with —OR$^{13}$, —NR$^{13}$R$^{14}$, —SR$^{13}$, or halogen;

$R^{13}$ and $R^{14}$ are each independently —H, —C$_1$-C$_6$ alkyl, —C$_2$-C$_6$ alkenyl, or —C$_2$-C$_6$ alkynyl;

$R^{12}$ is —OH, —H, —C$_1$-C$_6$ alkyl, —C$_2$-C$_6$ alkenyl, —C$_2$-C$_6$ alkynyl, —C$_3$-C$_7$ cycloalkyl, aryl, or 5- to 10-membered ring heteroaryl, wherein each alkyl, alkenyl, alkynyl, cycloalkyl, aryl, or heteroaryl is optionally substituted with —OR$^{13}$, —NR$^{13}$R$^{14}$, —SR$^{13}$, halogen, —COOH, or —COOR$^{11}$;

m, n, and o are each independently an integer in the range of 0 to 30; and the sum of m, n, and o is 0 to 30.

In some embodiments, the charged species is a compound of Formula IV:

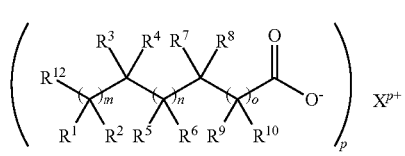

(Formula IV)

wherein:

$X^{p+}$ is a cationic counter ion having a charge state p, and p is 1, 2, or 3;

$R^1$, $R^2$, $R^3$, $R^4$, $R^5$, $R^6$, $R^7$, $R^8$, $R^9$, and $R^{10}$ are each independently —H, —OR$^{13}$, —NR$^{13}$R$^{14}$, —SR$^{13}$, halogen, —C$_1$-C$_6$ alkyl, —C$_2$-C$_6$ alkenyl, —C$_2$-C$_6$ alkynyl, —C$_3$-C$_7$ cycloalkyl, aryl, or 5- to 10-membered ring heteroaryl, wherein each alkyl, alkenyl, alkynyl, cycloalkyl, aryl, or heteroaryl is optionally substituted with —OR$^{13}$, —NR$^{13}$R$^{14}$, —SR$^{13}$, or halogen;

$R^{13}$ and $R^{14}$ are each independently —H, —C$_1$-C$_6$ alkyl, —C$_2$-C$_6$ alkenyl, or —C$_2$-C$_6$ alkynyl;

$R^{12}$ is —OH, —H, —C$_1$-C$_6$ alkyl, —C$_2$-C$_6$ alkenyl, —C$_2$-C$_6$ alkynyl, —C$_3$-C$_7$ cycloalkyl, aryl, or 5- to 10-membered ring heteroaryl, wherein each alkyl, alkenyl, alkynyl, cycloalkyl, aryl, or heteroaryl is optionally substituted with —OR$^{13}$, —NR$^{13}$R$^{14}$, —SR$^{13}$, halogen, —COOH, or —COOR$^{11}$;

m, n, and o are each independently an integer in the range of 0 to 30; and the sum of m, n, and o is 0 to 30.

In some embodiments, X is a lithium, sodium, potassium, calcium, barium, magnesium, or cesium ion.

In some embodiments, the charged species is a salt of a compound of Formula II:

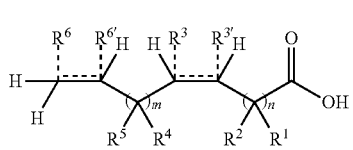

(Formula II)

wherein:

$R^1$, $R^2$, $R^4$, and $R^5$ are each independently —H, —OR$^{11}$, —NR$^{11}$R$^{12}$, —SR$^{11}$, halogen, —C$_1$-C$_6$ alkyl, —C$_2$-C$_6$ alkenyl, —C$_2$-C$_6$ alkynyl, —C$_3$-C$_7$ cycloalkyl, aryl, or 5- to 10-membered ring heteroaryl, wherein each alkyl, alkenyl, alkynyl, cycloalkyl, aryl, or heteroaryl is optionally substituted with —OR$^{11}$, —NR$^{11}$R$^{12}$, —SR$^{11}$, or halogen; R$^{11}$ and R$^{12}$ are each independently —H, —C$_1$-C$_6$ alkyl, —C$_2$-C$_6$ alkenyl, or —C$_2$-C$_6$ alkynyl;

the symbol ===== represents an optionally single or cis or trans double bond;

$R^3$ is —OH and $R^{3'}$ is selected from —H, —C$_1$-C$_6$ alkyl, —C$_2$-C$_6$ alkenyl, —C$_2$-C$_6$ alkynyl, —C$_3$-C$_7$ cycloalkyl, and aryl when ===== between $R^3$ and $R^{3'}$ is a single bond, and $R^3$ and $R^{3'}$ are absent when ===== between $R^3$ and $R^{3'}$ represents a double bond, $R^6$ is —OH and $R^{6'}$ is selected from —H, —C$_1$-C$_6$ alkyl, —C$_2$-C$_6$ alkenyl, —C$_2$-C$_6$ alkynyl, —C$_3$-C$_7$ cycloalkyl, and —C$_6$-C$_{10}$ aryl when ===== between $R^6$ and $R^{6'}$ is a single bond, and $R^6$ and $R^{6'}$ are absent when ===== between $R^6$ and $R^{6'}$ represents a double bond;

n is an integer in the range of 0 to 11;

m is an integer in the range of 0 to 25; and the sum of m and n is 0 to 25.

In some embodiments, the charged species is a compound of Formula V:

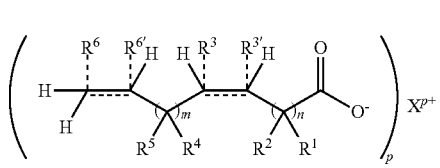

(Formula V)

wherein:

$X^{p+}$ is a cationic counter ion having a charge state p, and p is 1, 2, or 3;

$R^1$, $R^2$, $R^4$, and $R^5$ are each independently —H, —OR$^{11}$, —NR$^{11}$R$^{12}$, —SR$^{11}$, halogen, —C$_1$-C$_6$ alkyl, —C$_2$-C$_6$ alkenyl, —C$_2$-C$_6$ alkynyl, —C$_3$-C$_7$ cycloalkyl, aryl, or 5- to 10-membered ring heteroaryl, wherein each alkyl, alkenyl, alkynyl, cycloalkyl, aryl, or heteroaryl is optionally substituted with —OR$^{11}$, —NR$^{11}$R$^{12}$, —SR$^{11}$, or halogen;

$R^{11}$ and $R^{12}$ are each independently —H, —C$_1$-C$_6$ alkyl, —C$_2$-C$_6$ alkenyl, or —C$_2$-C$_6$ alkynyl;

the symbol ===== represents an optionally single or cis or trans double bond;

$R^3$ is —OH and $R^{3'}$ is selected from —H, —C$_1$-C$_6$ alkyl, —C$_2$-C$_6$ alkenyl, —C$_2$-C$_6$ alkynyl, —C$_3$-C$_7$ cycloalkyl, and aryl when ===== between $R^3$ and $R^{3'}$ is a single bond, and $R^3$ and $R^{3'}$ are absent when ===== between $R^3$ and $R^{3'}$ represents a double bond;

$R^6$ is —OH and $R^{6'}$ is selected from —H, —C$_1$-C$_6$ alkyl, —C$_2$-C$_6$ alkenyl, —C$_2$-C$_6$ alkynyl, —C$_3$-C$_7$ cycloalkyl, and —C$_6$-C$_{10}$ aryl when ===== between $R^6$ and $R^{6'}$ is a single bond, and $R^6$ and $R^{6'}$ are absent when ===== between $R^6$ and $R^{6'}$ represents a double bond;

n is an integer in the range of 0 to 11;

m is an integer in the range of 0 to 25; and the sum of m and n is 0 to 25.

In some embodiments, X is a lithium, sodium, potassium, calcium, barium, magnesium, or cesium ion.

In some embodiments, the charged species is a salt of a compound of Formula III:

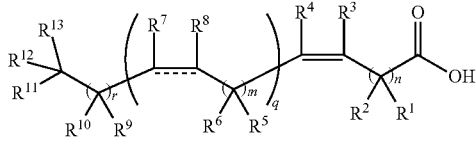

(Formula II)

wherein:

$R^1$, $R^2$, $R^5$, $R^6$, $R^9$, $R^{10}$, $R^{11}$, $R^{12}$, and $R^{13}$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkynyl, —C$_3$-C$_7$ cycloalkyl, aryl, or heteroaryl, wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen;

$R^3$, $R^4$, $R^7$, and $R^8$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkenyl, —C$_2$-C$_6$ alkynyl, —C$_3$-C$_7$ cycloalkyl, aryl, or heteroaryl wherein each alkyl, alkynyl, cycloalkyl, aryl, or heteroaryl is optionally substituted with one or more —OR$^{14}$, —NR$^{14}$R$^{15}$, —SR$^{14}$, or halogen;

$R^{14}$ and $R^{15}$ are each independently, at each occurrence, —H, —C$_1$-C$_6$ alkyl, —C$_2$-C$_6$ alkenyl, or —C$_2$-C$_6$ alkynyl;

the symbol ===== represents a single bond or a cis or trans double bond;

the symbol ===== represents a cis or trans double bond;

n is 0, 1, 2, 3, 4, 5, 6, 7, or 8;

m is 0, 1, 2, or 3; q is 0, 1, 2, 3, 4, or 5; and r is 0, 1, 2, 3, 4, 5, 6, 7, or 8.

In some embodiments, $R^3$ and $R^4$ combine with the carbon atoms to which they are attached to form a C$_3$-C$_6$ cycloalkyl, a C$_4$-C$_6$ cycloalkenyl, or a 3- to 6-membered ring heterocycle. In some embodiments, $R^7$ and $R^8$ combine with the carbon atoms to which they are attached to form a C$_3$-C$_6$ cycloalkyl, a C$_4$-C$_6$ cycloalkenyl, or a 3- to 6-membered ring heterocycle.

In some embodiments, the charged species is a compound of Formula VI:

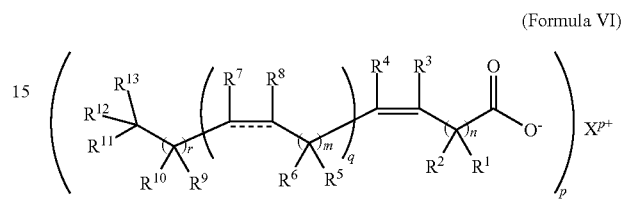

(Formula VI)

wherein:

$X^{p+}$ is a cationic counter ion having a charge state p, and p is 1, 2, or 3;

$R^1$, $R^2$, $R^5$, $R^6$, $R^9$, $R^{10}$, $R^{11}$, $R^{12}$, and $R^{13}$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkynyl, —C$_3$-C$_7$ cycloalkyl, aryl, or heteroaryl, wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen;

$R^3$, $R^4$, $R^7$, and $R^8$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkenyl, —C$_2$-C$_6$ alkynyl, —C$_3$-C$_7$ cycloalkyl, aryl, or heteroaryl, wherein each alkyl, alkynyl, cycloalkyl, aryl, or heteroaryl is optionally substituted with one or more —OR$^{14}$, —NR$^{14}$R$^{15}$, —SR$^{14}$, or halogen;

$R^{14}$ and $R^{15}$ are each independently, at each occurrence, —H, —C$_1$-C$_6$ alkyl, —C$_2$-C$_6$ alkenyl, or —C$_2$-C$_6$ alkynyl;

the symbol ===== represents a single bond or a cis or trans double bond;

the symbol ===== represents a cis or trans double bond;

n is 0, 1, 2, 3, 4, 5, 6, 7, or 8;

m is 0, 1, 2, or 3;

q is 0, 1, 2, 3, 4, or 5; and r is 0, 1, 2, 3, 4, 5, 6, 7, or 8.

In some embodiments, $R^3$ and $R^4$ combine with the carbon atoms to which they are attached to form a C$_3$-C$_6$ cycloalkyl, a C$_4$-C$_6$ cycloalkenyl, or a 3- to 6-membered ring heterocycle. In some embodiments, $R^7$ and $R^8$ combine with the carbon atoms to which they are attached to form a C$_3$-C$_6$ cycloalkyl, a C$_4$-C$_6$ cycloalkenyl, or a 3- to 6-membered ring heterocycle.

In some embodiments, X is a lithium, sodium, potassium, calcium, barium, magnesium, or cesium ion.

The identity of the charged species depends on the starting materials used in the methods described herein (e.g., polyethylene terephthalate, poly(2-hydroxybutarate), poly(caprolactone), poly(lactic acid), polyhydroxyalkanoates, nylons, aromatic polyamides, polyphthalamide). For example, when methods according to this disclosure are used in the depolymerization of polyethylene terephthalate, the resulting charged species will correspond to salt forms of, e.g., bis(2-hydroxyethyl)terephthalate, mono(2-hydroxyethyl)-terephthalic acid ester, terephthalic acid, ethylene glycol, and oligomers thereof.

Mechanical processes (including mechanical phenomena, such as friction, grinding, sonic, and potential energy) can be used to impart chemical change of compounds (e.g., a polyester- or polyamide-containing compound described herein) at the molecular level in mixtures. Mechanical processing can include milling techniques, such as ball milling techniques including planetary ball milling and attrition ball milling, as well as other grinding and agitation processes.

Grinding Processes

Grinding processes can include milling techniques. Examples of suitable milling techniques include ball milling, jet milling, roller milling, rotor milling, vibratory milling, hammer milling, impact milling, and media agitation milling (e.g. attrition milling). In some embodiments, the ball milling technique is planetary ball milling. In one example, a planetary ball mill spins two ceramic-lined chambers containing milling media and reactants at high spinning frequency. As the chambers spin, the media impacts the reactants and the sides of the chamber. The energy from these collisions, as well as the heat generated from friction, produces a high-energy environment that is capable of producing chemical change.

In some embodiments, the conversion of the first mixture to the second mixture, e.g., by decomposition (e.g., depolymerizing or hydrolyzing), occurs at an increased rate relative to a non-agitated sample. In some embodiments, conversion occurs at a rate of at least two or three times that of the non-ground sample. For example, grinding (e.g., milling) can occur at a spinning frequency sufficient to substantially depolymerize a condensation polymer. In some embodiments, conversion is greater with mechanical processing than without mechanical processing. The grinding can occur at a spinning frequency sufficient to hydrolyze a compound described herein (e.g., a polyester-containing compound described herein). The decomposition can occur at a faster rate than solvent based chemical depolymerization methods (e.g., at least 2, 3, 5, 7, or 10 times faster than decomposition using solvent-based chemical depolymerization methods).

Parameters for Grinding Processes

A mixture comprising a compound described herein (e.g., a polyester- or polyamide-containing compound) can be subjected to a grinding process for a sufficient time to substantially decompose said compound into decomposition products. In some embodiments, the time is less than 24 hours, and more than 1 minute. In some embodiments, the time is more than 5, 10, 30, or 60 minutes. In some embodiments, the time is 1 to 5, 1 to 10, 1 to 24, or 1 to 48 hours. In some embodiments, the time is 0.5 to 24, 5 to 20, 8 to 18, 10 to 15, or 11 to 13 hours.

A milling process described herein can occur at a spinning frequency of 1 to 1000, 250 to 1000, 500 to 1000, 500 to 800, or 600 to 750 rpm. Milling can also occur at a spinning frequency of at least 1, 250, 500, 550, 600, or 650 rpm.

Agitation Processes

A mechanical process can include agitation. Agitation processes include sonic agitation (including ultrasonic agitation) and attrition milling.

In some embodiments, the conversion of the first mixture to the second mixture by decomposition (e.g., depolymerizing or hydrolyzing) occurs at an increased rate relative to the non-agitated sample. In some instances, conversion occurs at a rate of at least two or three times that of the non-agitated sample. For example, agitation can occur at a spinning frequency sufficient to substantially depolymerize a condensation polymer. Conversion can be greater in the presence of mechanical processing than in the absence of mechanical processing. In some embodiments, agitation can occur at a spinning frequency sufficient to hydrolyze a polyester- or polyamide-containing compound. In some embodiments, decomposition occurs at a faster rate than solvent based chemical depolymerization methods.

Parameters for Agitation Processes

A mixture comprising a polyester-containing compound can be subjected to an agitation process for a sufficient time to substantially decompose the compound into constituent monomers. In some embodiments, the time is more than one minute and less than 24 hours. In some embodiments, the time is more than 5, 10, 30, or 60 minutes. In some embodiments, the time is 1 to 5, 1 to 10, 1 to 24, or 1 to 48 hours. In some embodiments, the time is 0.5 to 24, 5 to 20, 8 to 18, 10 to 15, or 11 to 13 hours.

In some embodiments, an agitation process can occur at a spinning frequency of 1 to 1000, 250 to 1000, 500 to 1000, 500 to 800, or 600 to 750 rpm. Attrition milling can also occur at a spinning frequency of at least 1, 250, 500, 550, 600, or 650 rpm.

Properties after Mechanical Processing

In some embodiments, the conversion (by mass) of a condensation polymer (e.g. a polyamide such as nylon, a polyester such as cutin, or polyethylene terephthalate) or a triglyceride to its respective depolymerization products, both as direct products of the decomposition and as byproducts, is greater in the presence of mechanical processes than in the absence of mechanical processes. In some embodiments, the method further comprises hydrolysis of the condensation polymer. In some embodiments, the conversion rate can be at least 5%, 10%, 20%, 30%, 40%, 50%, 60%, 70%, 80%, 90%, or 95%. Furthermore, of the resulting monomer, oligomer, ester and/or salt decomposition products, at least 50%, 60%, 70%, 80%, 90%, or 95% can be direct decomposition products (such as monomers, oligomers formed thereof, or in some embodiments, terephthalic acid and/or oligomers thereof). Substantial decomposition (e.g., depolymerization) of a compound (e.g., a polyester-containing compound) can be achieved without added thermal energy. Mechanical processing can also result in particle size reduction. A mechanical energy force applied to mixtures (e.g., by grinding, agitation, or milling, such as planetary milling or attrition milling) can result in particles that are less than about 1000, 500, 250, 100, 75, 50, 40, 30, 20, 10, 5, 2, or 1 micron in mean size. The mean particle size can be 0.1 to 1, 1 to 50, 1 to 100, 1 to 200, 1 to 250, 1 to 300, 1 to 350, 1 to 400, 1 to 500, 1 to 600, 1 to 700, 1 to 800, 1 to 900, or 1 to 1000 microns. The resulting particles may be of sufficiently small size to result in efficient dissolution in water or other solvents at a rate at least twice as fast as larger particles, allowing for fast mixing of solutions subsequently formed with the decomposition products.

Isolation of Monomers (Including Acidifying)

Decomposition products can be isolated from a mixture subjected to a mechanical process. Methods of isolation include acidification, distillation, filtration, melt filtration, precipitation, and centrifugation.

Examples of Acids

Acidifying can include adding an acid to the mixture. The acid can be an inorganic acid or an organic acid. In some embodiments, the acid is a strong acid, including an inorganic acid such as hydrochloric acid, sulfuric acid, or phosphoric acid. Examples of suitable acids include 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphor-10-sulfonic acid (+), capric acid (decanoic acid), caprylic acid (octanoic acid), cinnamic acid, citric acid, cyclamic acid, dodecylsulfuric acid, ethane-1,2-disulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, maleic acid, malic acid (−L), malonic acid, mandelic acid (DL), methanesulfonic acid, naphthalene-1, 5-disulfonic acid, naphthalene-2-sulfonic acid, nicotinic acid, nitric acid, oxalic acid, palmitic acid, pamoic acid, phosphoric acid, proprionic acid, pyroglutamic acid (−L), salicylic acid, sebacic acid, sorbic acid, succinic acid, sulfamic acid, sulfuric acid, tartaric acid (+L), thioacetic acid, trifluoroacetic acid, thiocyanic acid, and toluenesulfonic acid (p).

pH Ranges Provided by Acidifying

Acidifying can result in a solution with a pH of 5 or less, 3 or less, or 1 or less. The pH of the solution can be, for example, 0 to 4.5, 2 to 4, or 2.5 to 3.5. In some cases, the solution has a pH appropriate to fully neutralize any carboxylate salts.

Treatment Time (Acidifying)

A mixture comprising a compound described herein (e.g., a polyester- or polyamide-containing compound described herein) can be subjected to acidifying for a certain period of time, such as more than 1 minute and less than 24 hours (e.g., about 5 minutes to 24 hours. In some embodiments, the time is more than 5, 10, 30, or 60 minutes. In some embodiments, the time is 1 to 5, 1 to 10, 1 to 24, or 1 to 48 hours. In some embodiments, the time is 0.5 to 24, 5 to 20, 8 to 18, 10 to 15, or 11 to 13 hours.

Other Additional Steps of the Methods

Pretreatment Options for Starting Composition

Compounds described herein (e.g., a polyester- or polyamide containing compound described herein) may be first subjected to pretreatment conditions prior to treatment with a nucleophile and/or mechanical energy. As described above, to form a cutin-derived composition suitable for coating applications, cutin-containing portions of plant matter are first separated (or at least partially separated) from non-cutin-containing portions. This may be achieved by a number of methods, either alone or in combination with one another. For example, the plant matter may be thermally and/or mechanically and/or enzymatically and/or chemically treated to at least partially separate the cutin-containing portion from the non-cutin-containing portion. Or, the plant matter may be subjected to elevated temperature and/or pressure in an aqueous medium (e.g., as in pressure cooking) to partially separate the cutin-containing portion from the non-cutin-containing portion of the plant matter. Alternatively, the plant matter may be subjected to lower temperatures (e.g., as in freezing) to partially separate the cutin-containing portion from the non-cutin-containing portion of the plant matter. The plant matter may also be subjected to sonication in an aqueous medium to partially separate the cutin-containing portion from the non-cutin-containing portion of the plant matter. Optionally, the cutin-containing portion may be heated in a mixture of ammonium oxalate and oxalic acid to aid separation of the cutin-containing portion from the non-cutin-containing portion (e.g., the remainder of the cuticle and unwanted plant matter). Optionally, this separation may be achieved (or assisted) enzymatically using enzymes capable of hydrolyzing ester bonds and/or alternatively using enzymes capable of breaking down polysaccharides that comprise the non-cutin-containing portion of the plant. The cutin-containing portion may optionally be refluxed in at least one organic solvent (such as chloroform and/or methanol) to remove residual waxes and/or any remaining soluble components from the cutin. Alternatively, removal of residual waxes and remaining soluble components may be achieved using liquid or supercritical $CO_2$.

Additional Steps After Subjecting to Mechanical Processing

Decomposition products that result from a mechanical process can be chemically modified to provide derivatives with properties that can be tailored for specific applications. For example, oxygen and water barrier properties of subsequently formed coatings can be controlled by chemically modifying the decomposition products, and such modifications may require that the decomposition products first be protonated or rendered neutral. Furthermore, the chemical modification of the decomposition products can be tailored to change the solubility of the extract composition to allow for expanded options for coating deposition. In some cases, a mixture including free fatty acid and/or free fatty ester decomposition products is dissolved in another solvent to form a solution, thereby resulting in a composition suitable for coating applications (e.g., agricultural coating applications). Optionally, prior to forming the composition, the free fatty acid and/or free fatty ester decomposition products of the mixture are activated or modified (e.g., dehydroxylated, dehydrated, hydrogenated, or glycerated). For example, the free fatty acid and/or free fatty ester decomposition products can be modified to form a mixture of 1-monoacylglycerides and/or 2-monoacylglycerides, and the mixture of modified decomposition products (e.g., 1-monoacylglycerides and/or 2-monoacylglycerides) is dissolved in a solvent to form a solution, thereby resulting in the composition. In some embodiments, the isolated cutin-derived monomers are dehydroxylated to form a free fatty acid or ester free from any hydroxylation. One way to achieve this includes activation of the hydroxyl groups with different reagents or by a hydrothermal process, and subsequent elimination, followed by hydrogenation of the resulting unsaturation. These steps can be performed independently or concurrently in a process. These hydroxyl-free fatty acids or esters can then be modified, for example, to form a mixture of 1-monoacylglycerides and/or 2-monoacylglycerides, and the mixture of modified decomposition products (e.g., 1-monoacylglycerides and/or 2-monoacylglycerides) includes a mixture that can be dissolved in a solvent to form a solution, thereby resulting in the composition.

At least a portion of decomposition products that are isolated from the mixture can be esterified with a glycerol molecule. In some embodiments, the decomposition products are dehydrated. For example, esters (e.g., glyceryl esters) of direct depolymerization products (e.g., 100 or 101 in FIGS. 5A and 5B, respectively) can be formed via esterification (e.g., Fischer esterification or enzymatic esterification) following a mechanochemical depolymerization process. In some cases, the esterification results in dimers, trimers, oligomers, or fragments thereof. In one example, the esterified compound is a dimer with the structure:

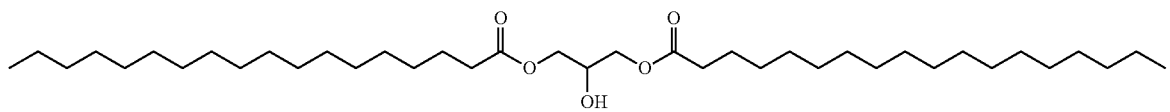 [SMILES: CCCCCCCCCCCCCCCCCC(=O)OCC(O)COC(=O)CCCCCCCCCCCCCCCCC]

The cutin depolymerization products may be purified, for example by selective filtering, distillation, and/or crystallization, to form an extract composition suitable for coating applications that is a substantially pure composition of direct decomposition products, such as the monomers in FIGS. 5A-5H (and/or oligomers formed thereof), or of esterified or glycerated compounds formed.

Figure 7A:
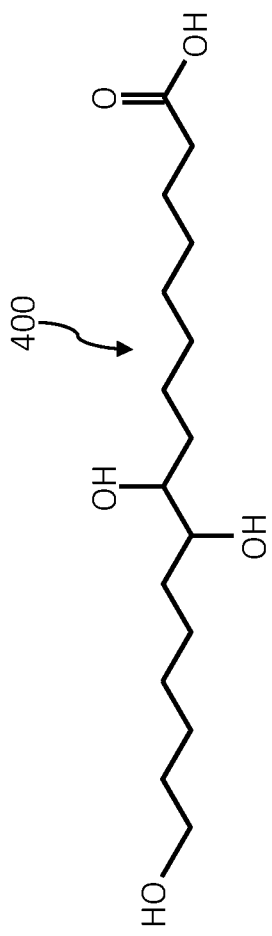
FIGS. 7A-7C show chemical structures of molecules formed from unsaturated indirect byproducts of depolymerization of cutin.
Figure 7B:
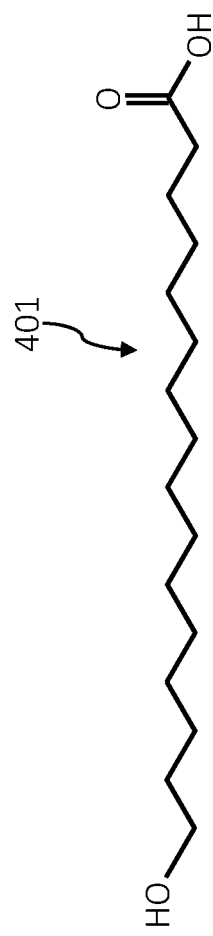
Figure 7C:
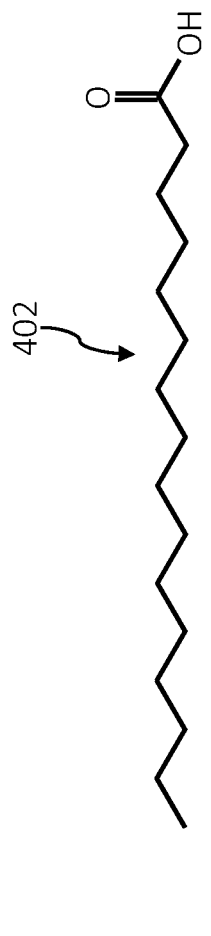
Figure 8:
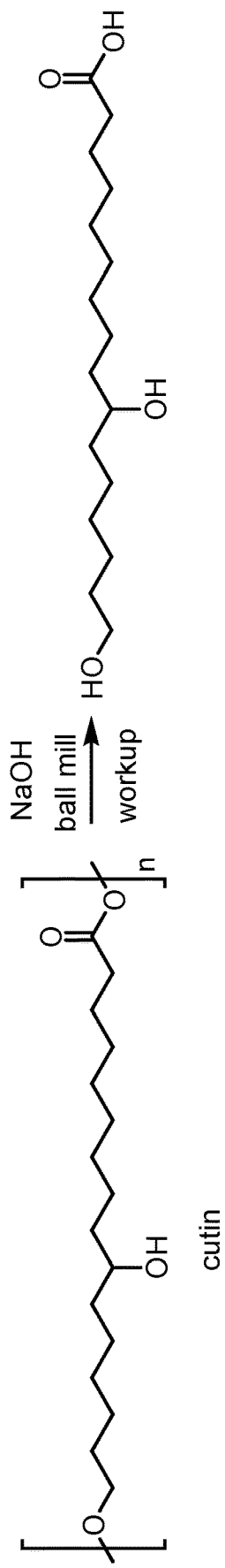
FIG. 8 shows a reaction scheme of the base catalyzed mechanochemical depolymerization of cutin in a ball mill to produce DHPA as the major product.

In some embodiments, some percentage (e.g., greater than 20%, 40%, 60%, 70%, 80%, or 90%) of the direct depolymerization products (e.g., monomers 100, 101, 102, 103, 104, 105, 106, and/or 107 depicted in FIGS. 5A-5H and/or include, for example, bis(2-hydroxyethyl)terephthalate, mono(2-hydroxyethyl)terephthalic acid ester, terephthalic acid, ethylene glycol, and oligomers thereof. As another example, for depolymerization of cutin, the resulting monomers can include hydroxy fatty acids, hydroxy fatty acid salts, and hydroxy fatty acid esters. For example, as depicted in FIG. 8, base-catalyzed mechanochemical depolymerization of cutin in a ball mill can produce 10,16-dihydroxyhexadecanoic acid as the major product. Additionally, oligomers, such as, e.g.,

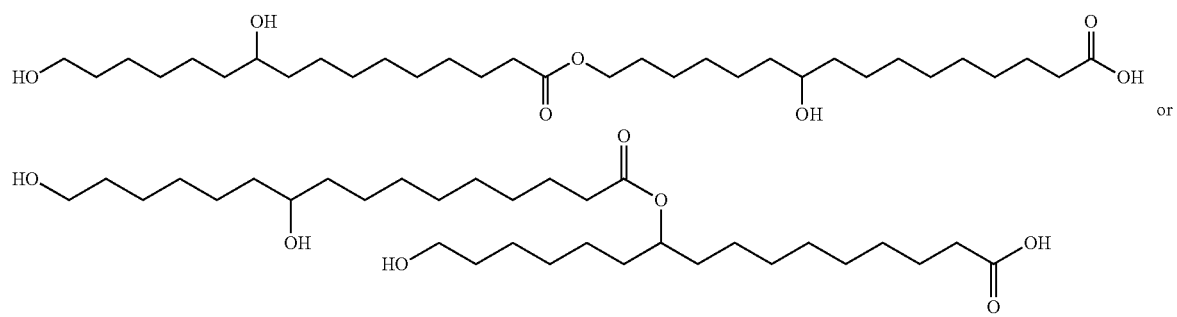

compounds of Formula I) to decompose into other monomer/oligomer byproducts (e.g., unsaturated byproducts 200, 201, 202, 203, 204, 205, 206, 207, and/or 208 of FIGS. 6A-6I, respectively) that do not typically result from the depolymerization of cutin or cutin-containing components. Specifically, the unsaturated byproducts 200, 201, 202, 203, 204, 205, 206, 207, and/or 208 of FIGS. 6A-6I, respectively, as well as the compounds of Formula II and III, may each be isolated and further processed, for example, by hydrogenation with a catalyst (e.g., Ni, Pd, or Pt) to form other saturated molecules such as those shown in FIGS. 7A-7C, where FIG. 7A is 9,10,16-trihydroxyhexadecanoic acid (400), FIG. 7B is 16-hydroxyhexadecanoic acid (401), and FIG. 7C is palmitic acid (402). In some cases, palmitic acid is formed from non-palm sources. This is significant at least because the production of palm oil from oil palms has a large environmental impact, including deforestation and habitat loss, as well as sociological impacts, since indigenous people are often displaced to make room for large plantations in the developing world.

End Products Produced by Methods

Methods according to this disclosure can yield carboxylic acids, carboxylic acid salts, carboxylic acid esters, alcohols, and/or amines as the constituent monomers. The identity of the monomer will depend on the identity of the polyester- or polyamide-containing feedstock, e.g., cutin, polyethylene terephthalate, poly(2-hydroxybutarate), poly(caprolactone), poly(lactic acid), and polyhydroxyalkanoates, as well as polyamides such as nylons, aromatic polyamides, and polyphthalamide. The end products correspond to the appropriate monomers and oligomers that characterize the polyesters and polyamides. For example, for depolymerization of polyethylene terephthalate, the resulting compounds can can be isolated from the depolymerization of cutin.

In some embodiments, the methods according to this disclosure are useful in the decomposition of triglycerides to yield, for example, glyceryl esters of fatty acids. The glyceryl ester can include the reaction product of glycerol and two fatty acids (i.e., 1,2-diglycerides and 1,3-diglycerides). In some embodiments, the glyceryl ester comprises the reaction product of glycerol and one fatty acid (i.e., 1-monoglycerides and 2-monoglycerides). The fatty acids can be saturated or unsaturated. In some embodiments, the fatty acids contain a carbon chain length of 7 or more carbon atoms (e.g., 7 to 22, or 16 to 18 carbon atoms). In some embodiments, the fatty acids are compounds of Formula I, Formula II, and/or Formula III.

Constituent Monomers of Formula I, Formula II, and Formula III

The methods described herein can yield an end product such as a constituent monomer of a compound (e.g., a polyester-containing compound). In some embodiments, the constituent monomer comprises at least one compound of Formula I, at least one compound of Formula II, at least one compound of Formula III, or any combination thereof.

In some embodiments, the constituent monomer of Formula I comprises one or more of:

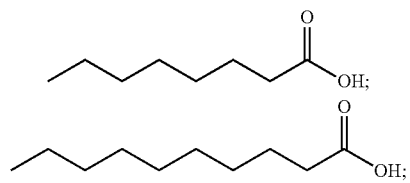

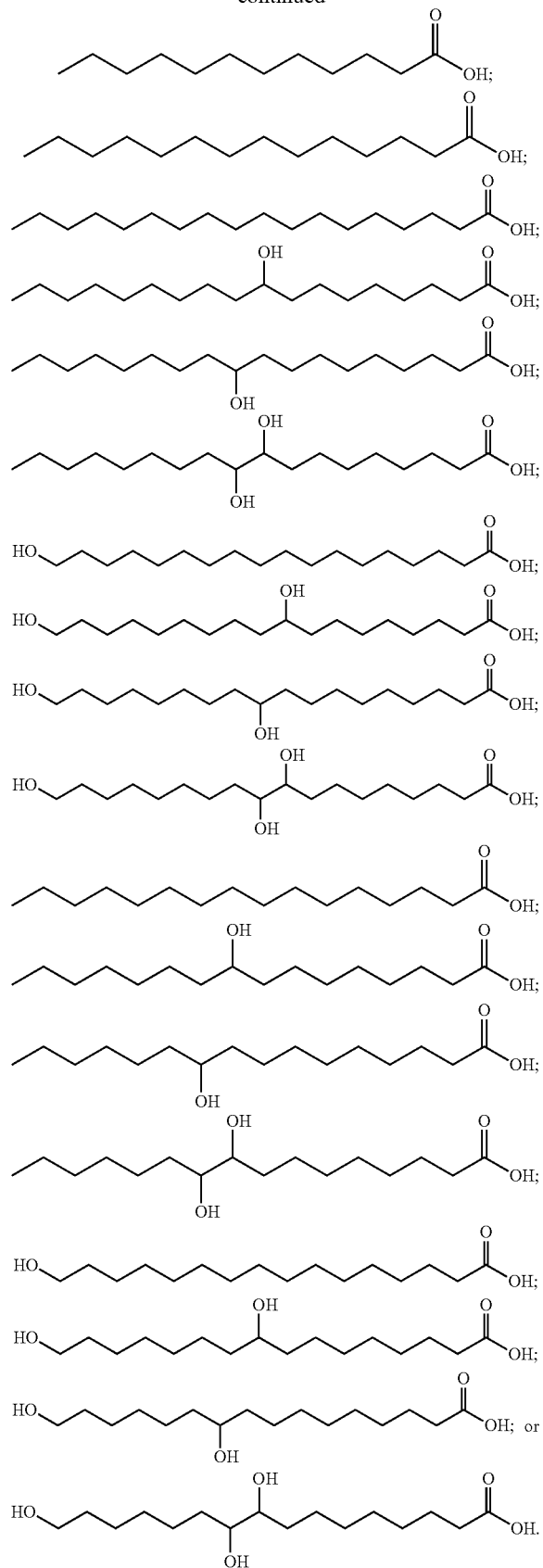

In some embodiments, the constituent monomer of Formula III comprises one or more of:

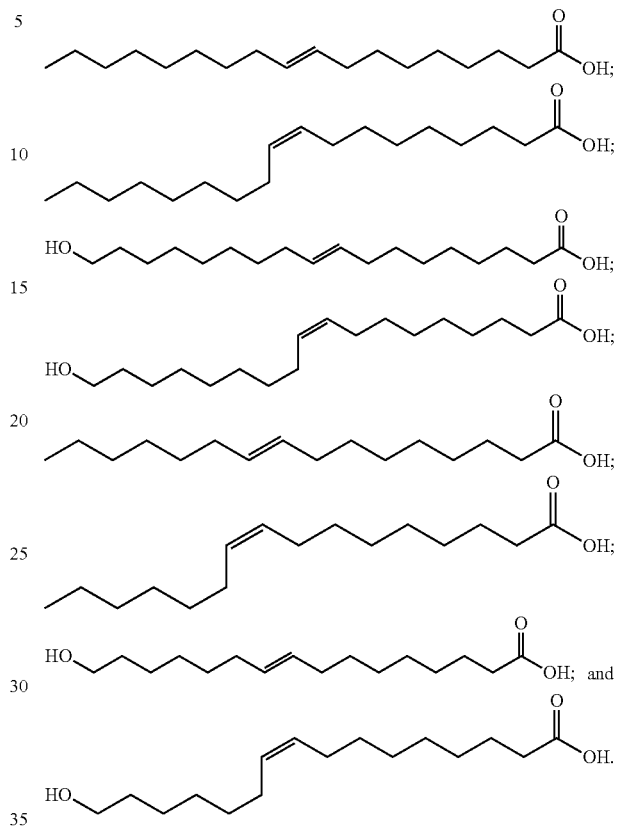

Conversion Rates

A constituent monomer of Formula I can be produced from a compound (e.g., a polyester-containing compound described herein) subjected to the methods described herein in a conversion rate of greater than 50%. In some embodiments, the conversion rate is about 55%, 60%, 65%, 70%, 75%, or 80%. In some embodiments, the conversion rate is about 80% to about 100%.

A constituent monomer of Formula II can be produced from a compound (e.g., a polyester-containing compound) subjected to the methods described herein in a conversion rate of greater than 50%. In some embodiments, the conversion rate is about 55%, 60%, 65%, 70%, 75%, or 80%. In some embodiments, the conversion rate is about 80% to 100%.

A constituent monomer of Formula III can be produced from a compound (e.g., a polyester-containing compound) subjected to the methods described herein in a conversion rate of greater than 50%. In some embodiments, the conversion rate is about 55%, 60%, 65%, 70%, 75%, or 80%. In some embodiments, the conversion rate is about 80% to 100%.

The saturated products (e.g., 100, 101, 102, 103, 104, 105, 106, and 107 of FIGS. 5A-5H, and/or compounds of Formula I) are cross-linked within the cutin layer and are thereby isolated into monomers, oligomers, or both directly via depolymerization reactions, whereas the unsaturated products (e.g., 200, 201, 202, 203, 204, 205, 206, 207, and 208 of FIGS. 6A-6H and/or products of Formula II and Formula III) are byproducts that are formed by decomposition of the direct products.

The unsaturated products (e.g., 200, 201, 202, 203, 204, 205, 206, 207, and 208 of FIGS. 6A-6H, products of Formula II, and/or products of Formula III) are indirect products formed by further subjecting cutin-derived monomers, oligomers, or combinations thereof to acidic or hydrothermal conditions. In other embodiments, the unsaturated products (e.g., 200, 201, 202, 203, 204, 205, 206, 207, and 208 of FIGS. 6A-6H, products of Formula II, and/or products of Formula III), are present in the cutin layer and thereby become constituents of the extract composition when the composition is formed by mechanochemical depolymerization and/or isolation methods. The production of these unsaturated products can be suppressed or inhibited when cutin depolymerization is carried out using traditional depolymerization methods (e.g., under basic conditions). Accordingly, the methods according to this disclosure can be useful for obtaining unsaturated products more directly than other solvent-based methods.

Direct products (e.g., 100, 101, 102, 103, 104, and/or 105 of FIGS. 5A-5F and/or compounds of Formula I) but not the indirect unsaturated byproducts (e.g., 200, 201, 202, 203, 204, 205, 206, 207, and 208 of FIGS. 6A-6I, products of Formula II, and/or products of Formula III) of the cutin depolymerization can be present in the second mixture resulting from the decomposition (e.g., elimination) of the direct products. For example, when the monomer and/or oligomer products are isolated from the second mixture and subsequently used to form a protective coating, the coating can have desirable qualities (e.g., higher cross-link density, lower permeability to water and/or oxygen) when the second mixture includes a large fraction of saturated depolymerization products (e.g., 100, 101, 102, 103, 104, and/or 105 of FIGS. 5A-5F) while having as small a concentration as possible of the unsaturated indirect byproducts (e.g., 200, 201, 202, 203, 204, 205, 206, 207, and 208 of FIGS. 6A-6I and/or products of Formula II). In some embodiments, the indirect unsaturated byproducts (e.g., 200, 201, 202, 203, 204, 205, 206, 207, and 208 of FIGS. 6A-6H, products of Formula II and/or products of Formula III) are present in the resulting mixture in an amount of less than 30%, 25%, 20%, 15%, 10%, or 5%. In some embodiments, the unsaturated products are converted to the saturated products.

Protective Coatings

The resulting compounds (e.g., constituent monomers of polyester-containing compounds described herein, e.g., polyester-containing compounds extracted from plants) can be used to produce compositions (e.g., plant extract compositions) for protective coatings for applications such as food packaging. Compositions for forming protective coatings may subsequently be formed from any of the molecules 100, 101, 102, 103, 104, and 105 of FIGS. 5A-5F, and 400, 401, and 402 in 7A-7C, respectively, as well as any other direct decomposition products (e.g., compounds of Formula I). The coatings can be formed primarily from one of these types of molecules or from a combination of these molecules. In other embodiments, the compounds produced by the methods described herein may subsequently be esterified (e.g., glycerated to form 1-monoacyglycerides and/or 2-monoacylglycerides). The compositions to be used in the coatings can be formed from the esters or glycerated molecules, and the coatings can be formed from the esters or glycerated molecules in the compositions. The esters or glycerated molecules can be further combined with one or more fatty acid salts to form a composition to be used as a protective coating. The one or more fatty acid salts can be obtained as a depolymerization/decomposition product of polyester-containing compounds, or by the saponification of the esters and/or fatty acids produced by the methods according to this disclosure. Forming coatings from compositions formed from molecules 400 or from molecules 401 of FIG. 7A or 7B, respectively, or from a combination of molecules 100, 101, 102, 103, 104, and 105 of FIGS. 5A-5F, and 400, 401, and 402 of FIGS. 5A-5C, or from esters or glycerated molecules formed thereof, may allow for further control over the properties of both the extract compositions and the coatings. For example, the solubility of molecules 400, 401, and 402 of FIGS. 7A-7C (and esters, glycerated molecules, or salts formed thereof) in various solvents is different than that for molecules 100, 101, 102, 103, 104, and 105 of FIGS. 5A-5F (and esters, glycerated molecules, or salts formed thereof). As such, a wider variety of solvents may be available for use in forming compositions from molecules 400, 401, and 402 of FIGS. 7A-7C (or esters, glycerated molecules, or salts formed thereof), or from combinations of molecules 100, 101, 102, 103, 104, and 105 of FIGS. 5A-5F, and 400, 401, and 402 of FIGS. 7A-7C (or esters, glycerated molecules, or salts formed thereof), than may be used for compositions which only include substantial quantities of direct products and/or byproducts of cutin depolymerization (e.g., molecules 100, 101, 102, 103, 104, and 105 of FIGS. 5A-5F or esters, glycerated molecules, or salts formed thereof). Furthermore, properties of the coatings formed from the compositions can further be tailored for specific applications using molecules 400, 401, and/or 402 of FIGS. 7A and 7B (and/or esters, glycerated molecules or salts formed thereof), either alone or in combination with molecules 100, 101, 102, 103, 104, and/or 105 of FIGS. 5A-5F, and/or one another. For example, the crosslink density of the resulting protective films can vary depending on the percent mass of each of molecules 100, 101, 102, 103, 104, and 105 of FIGS. 5A-5F, and 400, 401, or 402 of FIGS. 7A-7C (and/or esters, glycerated molecules, or salts formed thereof) in the compositions, that allow for film properties such as density and permeability to be tailored for the specific application in which the film is used. Furthermore, these molecules can be chemically modified to tailor their properties, e.g., solubility, stability, and film-forming properties.

The molecules/compounds obtained directly from decomposition (e.g., compounds 100, 101, 102, 103, 104, or 105 of FIGS. 5A-5F) or indirectly through subsequent processing steps (e.g., compounds 400, 401, or 402 FIGS. 7A-7C) are glycerated to form 1-monoacylclyceride and/or 2-monoacylglyceride monomers, oligomers formed thereof, or combinations. In this case, the compositions (e.g., plant extract compositions) from which protective coatings are subsequently formed include the 1-monoacylclycerides and/or 2-monoacylglycerides optionally dissolved in a solvent. The difference between a 1-monoacylclyceride and a 2-monoacylglyceride is the point of connection of the glyceride group. Protective coatings formed over substrates such as agricultural products (e.g., fruits, vegetables, eggs, etc.) from formulations that include combinations of one or more 1-monoacylglycerides and optionally one or more 2-monoacylclycerides (or optionally a different additive, such as a fatty acid, fatty acid salt, or fatty acid ester, in place of the 2-monoacylclycerides) can exhibit superior performance in preventing water loss and oxidation from agricultural products without altering the physical appearance of the substrate.

A protective coating can be formed from the compositions obtained from a method described herein. The following is an exemplary embodiment for the production of the protective coating from a composition comprising a compound produced by the methods described herein (e.g., a constituent monomer of a polyester-containing compound, e.g., a constituent monomer of a polyester-containing compound derived from plant matter, e.g., a polyester-containing compound such as cutin or triglycerides). First, a solid mixture of the constituent monomers, oligomers, or both is dissolved in a solvent (e.g., water, ethanol, or combinations thereof) to form the composition. The concentration of the solid mixture in the solvent may, for example, be 0.1 to 100 mg/mL. Next, the solution that includes the constituent monomers, oligomers, or both is applied over the surface of the substrate to be coated, for example, by spray coating the substrate, by dipping the substrate in the solution, or by transfer from a brush bed. After applying the solution to the substrate, the substrate is allowed to dry or is actively dried until all of the solvent has evaporated, thereby allowing a coating composed of the monomer and/or oligomer units to form over the surface of the substrate.

The coatings formed from the monomers, oligomers, or both produced by the methods described herein can prevent water loss and shield agricultural products from threats such as bacteria, fungi, viruses, and the like. The coatings can also protect, for instance, plants and food products from physical damage (e.g., bruising), water loss, oxidation, and photodamage. Accordingly, the compositions, solutions, and coatings can be used to help store agricultural products for extended periods of time without spoiling. The compositions and coatings formed from the monomers and oligomers can also be edible (i.e., the coatings can be non-toxic). The methods for forming the coatings can be entirely organic (e.g. in compliance with 7 CFR 205, EEC 834/2007, and/or other applicable regulations). The coatings can be tasteless, colorless, and/or odorless. The coatings can be made from the same chemical feedstock that is naturally found in the plant cuticle, (e.g., hydroxy and/or dihydroxy palmitic acids, and/or hydroxy oleic and stearic acids) or extracted from the seed, bean, nut, kernel, or pulp material of plant matter (e.g., triglycerides, diglycerides, and monoglycerides) and can thus be organic and all-natural.

A composition is formed from cutin-derived monomers and/or oligomers and/or esters thereof extracted from cutin of a first plant species (e.g., utilizing the mechanochemical decomposition processes previously described), and the composition is then disposed over plant matter of the same plant species, such that the extracted monomers and/or oligomers and/or esters form a protective coating over the plant matter of the first plant species. Such a coating may, for example, reinforce the cuticle layer that naturally exists over the plant matter. In other embodiments, a composition is formed from cutin-derived monomers and/or oligomers and/or esters extracted from cutin of a first plant species (e.g., utilizing a mechanochemical decomposition process), and the composition is then disposed over plant matter of a second plant species which is different from (although in some cases could be the same as) the first plant species, such that the extracted monomers and/or oligomers and/or esters form a protective coating over the plant matter of the second plant species. For example, the composition may be formed from monomers and/or oligomers and/or esters extracted from cutin obtained from tomato or cranberry skins and then applied over strawberries, bananas, finger limes, lemons, or other plant species different from the plant species from which the cutin was obtained in order to form a protective coating. In other embodiments, a composition is formed from triglyceride-derived monomers and/or oligomers and/or esters extracted from the seed, bean, nut, kernel, or pulp material of plant matter from a first plant species (e.g., utilizing the mechanochemical decomposition process described herein), and the composition is then disposed over plant matter of the same type, or a different type of second plant species, such that the extracted monomers and/or oligomers and/or esters form a protective coating over the plant matter. The protective coatings that are formed from the monomers and/or oligomers and/or esters of the composition can provide forms of protection against biotic and abiotic stressors for which the native cuticle layer of the second plant species is inherently incapable of providing. For example, the protective coatings deposited over the substrates can provide superior protection against water loss and oxidation than may be inherently provided by the native cuticle layer. In some embodiments, the compositions can be formulated to inhibit or provide protection against fungal growth, for which the native cuticle layer provides little or no protection. The cutin-derived monomers and/or oligomers can be glycerated to form monoacylglycerides prior to the composition being disposed over the plant matter to form the coating. This may, for example, increase the reactivity of the monomers and/or oligomers and allow them to cross-link after being disposed over the plant matter.

Figure 5A:
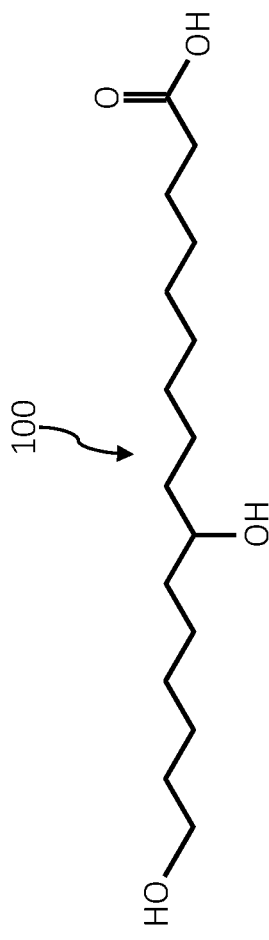
FIGS. 5A-5H show chemical structures of 10,16-dihydroxyhexadecanoic acid, 10,18-dihydroxyoctadecanoic acid, 9,16-dihydroxyhexadecanoic acid, 9,18-dihydroxyoctadecanoic acid, 9,10,16-trihydroxyhexadecanoic acid, 9,10,18-trihydroxyoctadecanoic acid, 9,10-epoxy-16-hydroxyhexadecanoic acid, and 9,10-epoxy-18-hydroxyhexadecanoic acid, respectively.
Figure 5B:
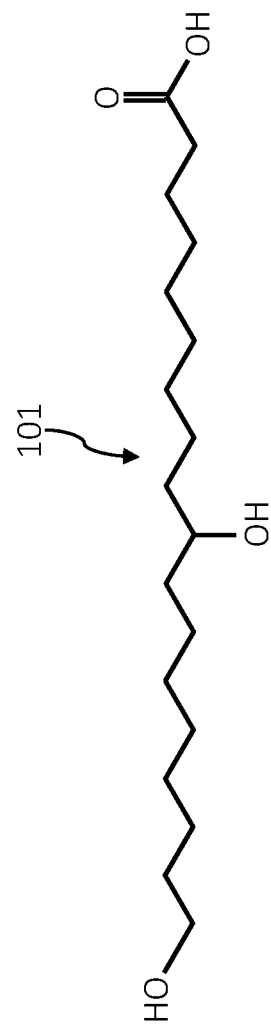
Figure 5C:
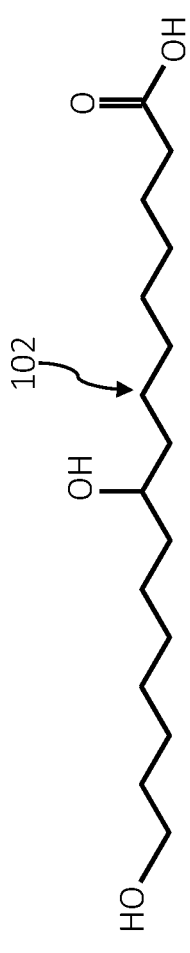
Figure 5D:
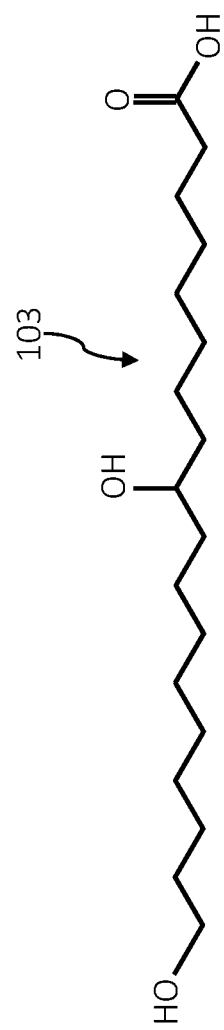
Figure 5E:
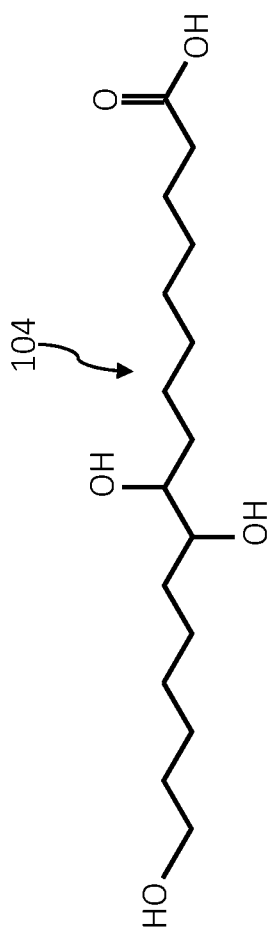
Figure 5F:
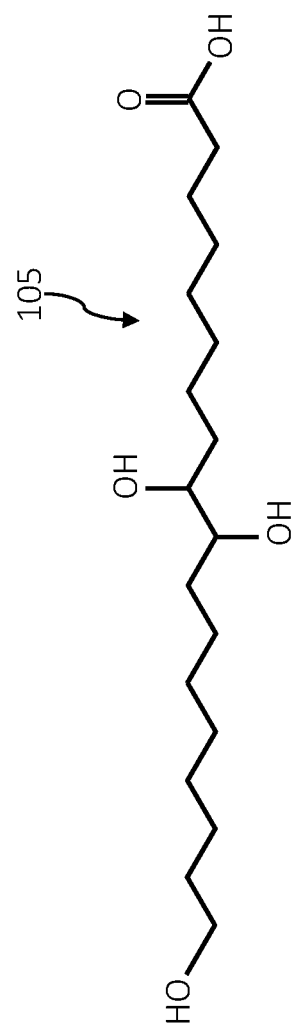
Figure 5G:
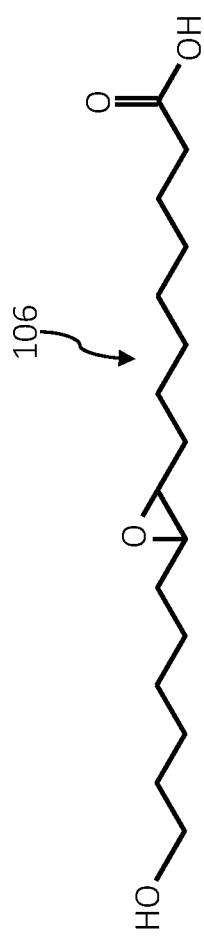
Figure 5H:
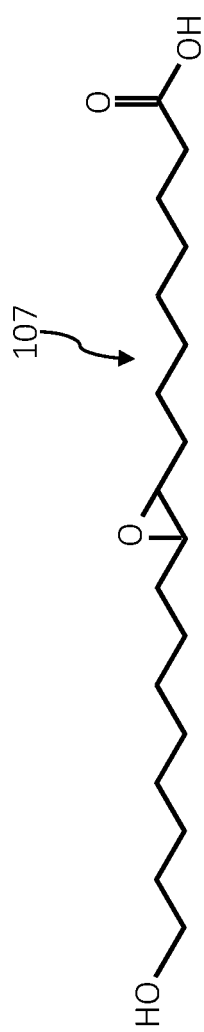
Figure 6A:
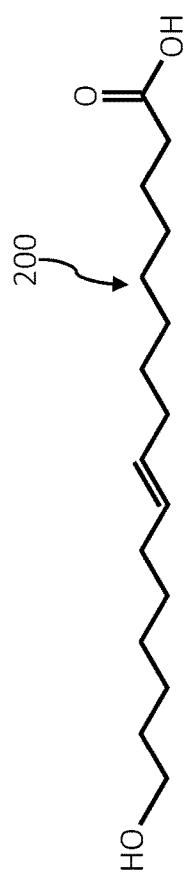
FIGS. 6A-6I show chemical structures of byproducts from the decomposition of 10,16-dihydroxyhexadecanoic acid monomers, and/or oligomers.
Figure 6B:
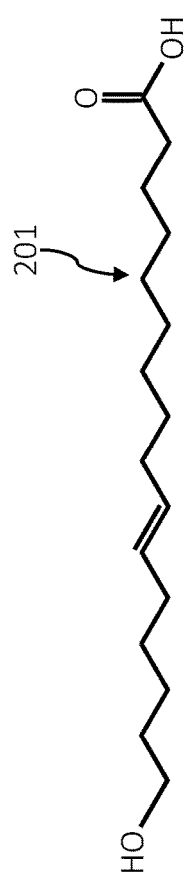
Figure 6C:
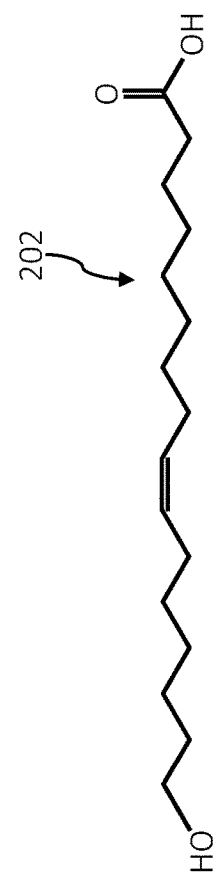
Figure 6D:
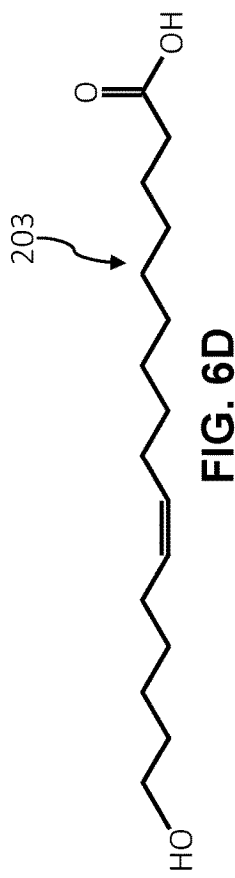
Figure 6E:
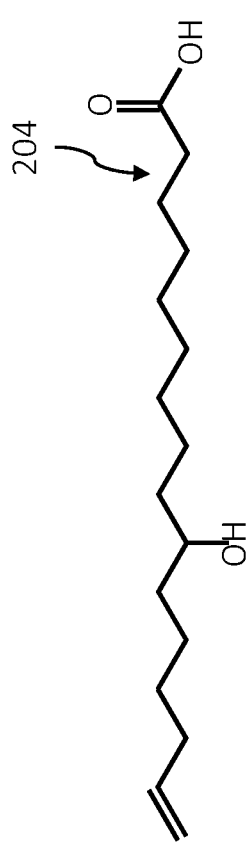
Figure 6F:
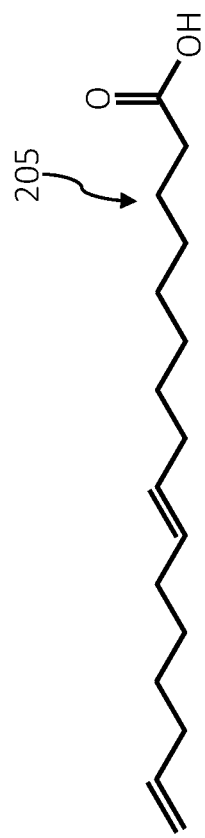
Figure 6G:
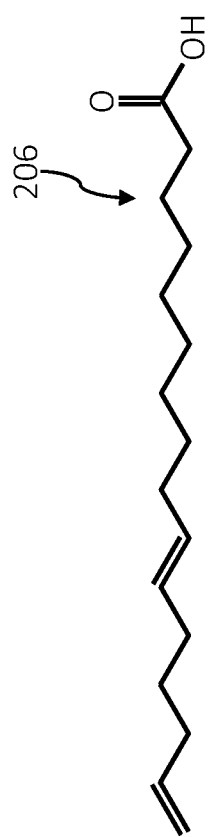
Figure 6H:
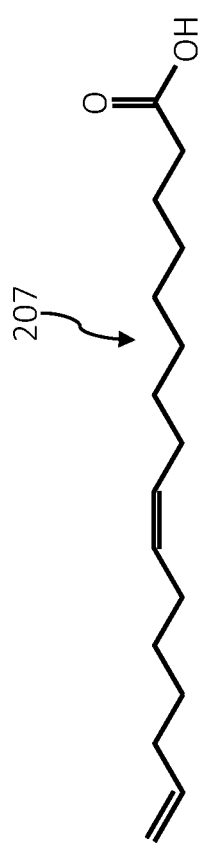
Figure 6I:
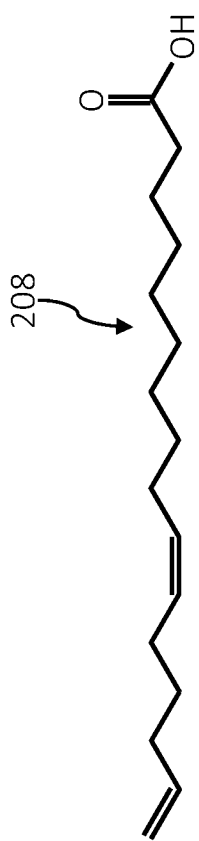

Saturated products of the decomposition reactions such as, for instance, free fatty acid compounds 100 and 101 in FIG. 5A and FIG. 5B, respectively, can be separated or at least partially separated from the unsaturated products (or byproducts) of the decomposition reactions (e.g., unsaturated fatty acid compounds in FIGS. 6A-6I). Separation or partial separation of the different types of reaction products can be used to purify, for instance, the saturated products (e.g., compounds wherein hydroxy groups have not been eliminated). In other words, extracting the crude products of a mechanochemical decomposition reaction can be used to purify or enrich the percentage of a given product depending on the solvent used.

Fiber-Based Materials

Compounds produced by methods of this disclosure (e.g., constituent monomers of polyester-containing compounds described herein, e.g., polyester-containing compounds extracted from plants) can be used to modify the properties of fiber-based materials, such as textiles, paper products, packaging materials, polymer materials, and the like. Compounds produced by methods of this disclosure are associated with one or more fibers of a fiber-based material. The association of one or more fibers of a fiber-based material with one or more compounds allows for properties of the resulting fiber-based material, such as hydrophobicity, hydrophilicity, lipophobicity, lipophilicity, omniphobicity, gas impermeability, and the like, to be tuned. The fiber can be, for example, cellulose, acrylic, kevlar, modacrylic, nomex, nylon, polyester, polyethylene, polypropylene, polycarbonates, polyamides, spandex, rayon, abaca, acetate, aloe vera, bamboo, baba, kapok, coir, corn, flax, hemp, jute, kenaf, lyocell, modal, pina, raffia, ramie, rayon, sisal, seacell, lenpur, lyocell, soy protein, pineapple, alpaca, angora wool, azlon, byssus, camel hair, cashmere wool, chiengora, lambswool, llama, mohair wool, qiviut, rabbit, silk, vicuna, wool, and yak fiber. In some embodiments, the fiber is nylon, polyester, polyethylene, polypropylene, a polycarbonate, a polyamide, or cellulose fiber.

During the manufacturing process of fiber-based materials, one or more compounds produced by the methods of this disclosure can be combined with one or more fibers (e.g., during the pulping phase of paper and/or packaging material or other fiber-based material manufacturing, or to a collection of, for example, individual fibers prior to weaving the fibers into a textile) so as to coat the fibers with the one or more compounds. In other embodiments, a prefabricated fiber-based material (e.g., paper, packaging materials, textiles or other fiber-based material) can be coated with the compounds so as to coat the fiber-based material with the one or more compounds. The fibers and pre-fabricated fiber-based materials can be combined with the one or more compounds using known methods. For example, the one or more fibers can be combined with one or more compounds and a solvent. The solvent can then be removed from the fibers to form a coating comprising the one or more compounds on the surface of the one or more fibers. As another example, the one or more compounds can be added to a solvent to form an emulsion or solution. Subsequently, the emulsion or solution can be applied to the surface of a pre-fabricated fiber based material, for example, by spraying, brushing, dipping, electrospraying, or pouring the emulsion or solution on the surface of the fiber-based material. Subsequently, the solvent can be removed to form a coating comprising the one or more compounds on the surface of the fiber-based material.

The compounds obtained using methods according to this disclosure can be amenable to polymerization. In some embodiments, the compounds are w-hydroxy fatty acids that can be polymerized to form a polyester. The w-hydroxy fatty acids can be polymerized with one or more other monomers (e.g., poly-hydroxy alcohols, carboxylic acids, dicarboxylic acids, oxo dicarboxylic acids, polyamines, diamides, adipoyl chlorides, and/or diisocyanates) to form a polymer. The one or more other monomers can be compounds obtained using the methods of this disclosure. In some embodiments, the one or more other monomers are other synthetic or commercially available monomers.

The polymerization of the compounds formed by the mechanochemical processes can be accomplished using known methods. In some embodiments, one or more compounds and optionally one or more synthetic or commercially available monomers are heated to an elevated temperature in the absence of a solvent to induce polymerization. In some embodiments, one or more compounds and optionally one or more synthetic or commercially available monomers are heated to an elevated temperature in the presence of a solvent to induce polymerization. Suitable solvents include water, alcohols, ethers, amines, hydrocarbons, or any combinations thereof. The polymerization can carried out in the presence of or in the absence of a polymerization catalyst.

In some embodiments, the compounds are polymerized in the presence of one or more fibers of fiber-based materials so as to tune the properties of the resulting fiber-based material. The one or more compounds can be combined with one or more fibers (e.g., during the pulping phase of paper and/or packaging material or other fiber-based material manufacturing, or to a collection of, for example, individual fibers prior to weaving the fibers into a textile), and subsequently polymerized so as to form a fiber-based material wherein the fibers are intercalated with a polymer. In other embodiments, a prefabricated fiber-based material (e.g., paper, packaging materials, textiles, or other fiber-based material) can be coated with the compounds and subsequently heated to induce polymerization of the compounds, resulting in a fiber-based material coated with a polymer.

EXAMPLES

The following examples describe condensation polymer-derived compositions and methods for obtaining the same. In each of the examples below, all reagents and solvents were purchased and used without further purification unless specified. All reactions were carried out under an atmosphere of nitrogen with commercial grade solvents unless otherwise stated. Reactions were monitored by thin layer chromatography (TLC) carried out on 0.25 mm E. Merck silica gel plates (60 Å, F-254) using UV light as the visualizing agent and an acidic mixture of anisaldehyde, ceric ammonium molybdate, or basic aqueous potassium permanganate ($KMnO_4$), and heat as developing agents. NMR spectra were recorded on a Bruker Avance 500 MHz and/or Varian VNMRs 600 MHz instruments and calibrated using residual un-deuterated solvent as an internal reference (e.g. $CHCl_3$ @ 7.26 ppm $^1H$ NMR). IR spectroscopy was performed on a Shimadzu IRSpirit with a QATR-S accessory. Ball milling was performed in a Retsch PM 200 planetary ball mill using yttria stabilized zirconium oxide (sometime referred to as YSZ, $ZrO_2$, zirconium oxide, zirconia, or 'ceramic') media in 50 mL yttria stabilized zirconium oxide jars, unless otherwise specified.

Abbreviations Used

EtOAc ethyl acetate
GPC gel permeation chromatography
DHPA dihydroxy palmitic acid or 10,16-dihydroxyhexadecanoic acid
PA palmitic acid Example 1: Method for Preparing Tomato Pomace Prior to Depolymerization Tomato pomace obtained from a commercial tomato processing facility was milled in a cutting mill and sifted to give different particle size distributions (e.g., >500 µm, 250-500 µm, 125-250 µm, etc.). The fraction corresponding to 250-500 µm was sequentially extracted with $CHCl_3$ overnight in a Soxhlet extractor and with methanol overnight in a Soxhlet extractor to remove the surface waxes and other soluble components, followed by drying under vacuum (<1 torr). The washed pomace was lyophilized overnight (<0.02 torr) to remove water, and then stored in a desiccator before use.

Example 2: Screening Catalysts for the Mechanochemical Depolymerization of Tomato Pomace A general procedure for the mechanochemical depolymerization of tomato cutin with different catalysts in a ball mill is as follows: A grinding jar was charged with dry tomato peel (1 g, 250-500 µm, 1 equiv. w/w) and 40 g of zirconium oxide media, and the resulting mixture was ground in a planetary ball mill (1 h, 650 rpm). A catalyst, and in some instances water, was added and the resulting mixture was ground in the planetary ball mill for the reaction times indicated in Table 1. After completion of the reaction, the mixture was diluted in $H_2O$ (100 mL), filtered, and the filtrate collected. If base was used, the filtrate was further treated with 3M HCl until a solution of pH 3 was obtained. The resulting aqueous solution was extracted with EtOAc (150 mL), and the separated EtOAc phase dried and analyzed by $^1H$ NMR.

TABLE 1

Effect of Catalysts on the Depolymerization of Tomato Cutin

| Entry | Catalyst | $H_2O$ Loading (mmol) | Catalyst Loading (mmol) | Crude Mass Recovery (g) | Reaction Time (h) | Major Product |
|---|---|---|---|---|---|---|
| 1 | NaOH | — | 13.2 | 0.48 | 12 | DHPA |
| 2 | NaOH | — | 13.2 | 0.40 | 1 | DHPA |
| 3 | NaOH | — | 6.6 | 0.28 | 12 | DHPA |
| 4 | KOH | — | 13.2 | 0.27 | 1 | DHPA |
| 5 | NaOH | 41.6 | 13.2 | 0.28 | 12 | DHPA |
| 6 | LiOH | — | 13.2 | 0.04 | 1 | — |
| 7 | $ZnSO_4 \cdot 7H_2O$ | 12.1 | 3.5 | 0.04 | 12 | oligomer |
| 8 | TsOH | 12.1 | 5.2 | 0.14 | 12 | unsat. PA/ oligomer |
| 9 | $Na_2CO_3$ | 41.6 | 13.2 | 0.05 | 12 | unsat. PA/ oligomer |
| 10 | TsOH | 41.6 | 13.2 | 0.05 | 12 | unsat. PA/ oligomer |
| 11 | $ZnSO_4$ $7H_2O$ | 41.6 | 3.5 | 0.04 | 12 | Oligomer |
| 12 | $H_2SO_4$ | 41.6 | 1.88 | 0.03 | 12 | unsat. PA |

The results demonstrate that acid catalysts promote alcohol elimination/oligomerization, which may allow for access to unsaturated compounds. The results demonstrate that hydroxide bases are more selective for depolymerization.

Example 3: Sodium Hydroxide Catalyzed Ball Milling Depolymerization of Tomato Pomace NaOH catalyzed ball milling depolymerization of tomato pomace was performed as follows: A grinding jar was charged with tomato pomace (1 g, 1 equiv. w/w), NaOH (0.5 g, 0.5 equiv. w/w), and 40 g of zirconium oxide media. The resulting mixture was ground in a planetary ball mill (650 rpm, 1 h). After 1 h, the ball mill was stopped, the jar rinsed with water (~150 mL) and acidified with aqueous 3 M HCl until pH 3 was obtained. The aqueous phase was extracted with EtOAc (150 mL), and the EtOAc phase collected and dried to give DHPA (0.3847 g, 38%) by $^1$H NMR and GPC analysis.

Example 4: Reaction Time

The reaction time was varied to determine the impact of time on the degree of depolymerization and recovery yield. All experiments were run at 650 rpm in a planetary ball mill and employed 1 g of dry tomato pomace, 40 g zirconium oxide media, and 3 g of NaOH. Reaction times of 0.5 h, 1 h, 3 h, 6 h, and 12 h were evaluated. The results are summarized in Table 2 and plotted in FIG. 1 compared to traditional base hydrolysis. In general, longer reaction times resulted in a higher degree of depolymerization. Overall, a reaction time of 12 hours led to optimal monomer contribution and recovery yield by GPC analysis.

TABLE 2

Effect of reaction time on degree of depolymerization

| Entry | Time (hours) | Recovery (mass recovered/ starting mass) | Product Distribution (GPC) |
|---|---|---|---|
| 1 | 0.5 | 33% | significant dimer, trimer, and oligomer peaks |
| 2 | 1 | 31% | major monomer peak, minor dimer and oligomer peaks |
| 3 | 3 | 37% | major monomer peak, minor dimer peak and very small, oligomer peak |
| 4 | 6 | 33% | major monomer peak and very small dimer peak |
| 5 | 12 | 43% | monomer only |

Example 5. Base Strength

Figure 2:
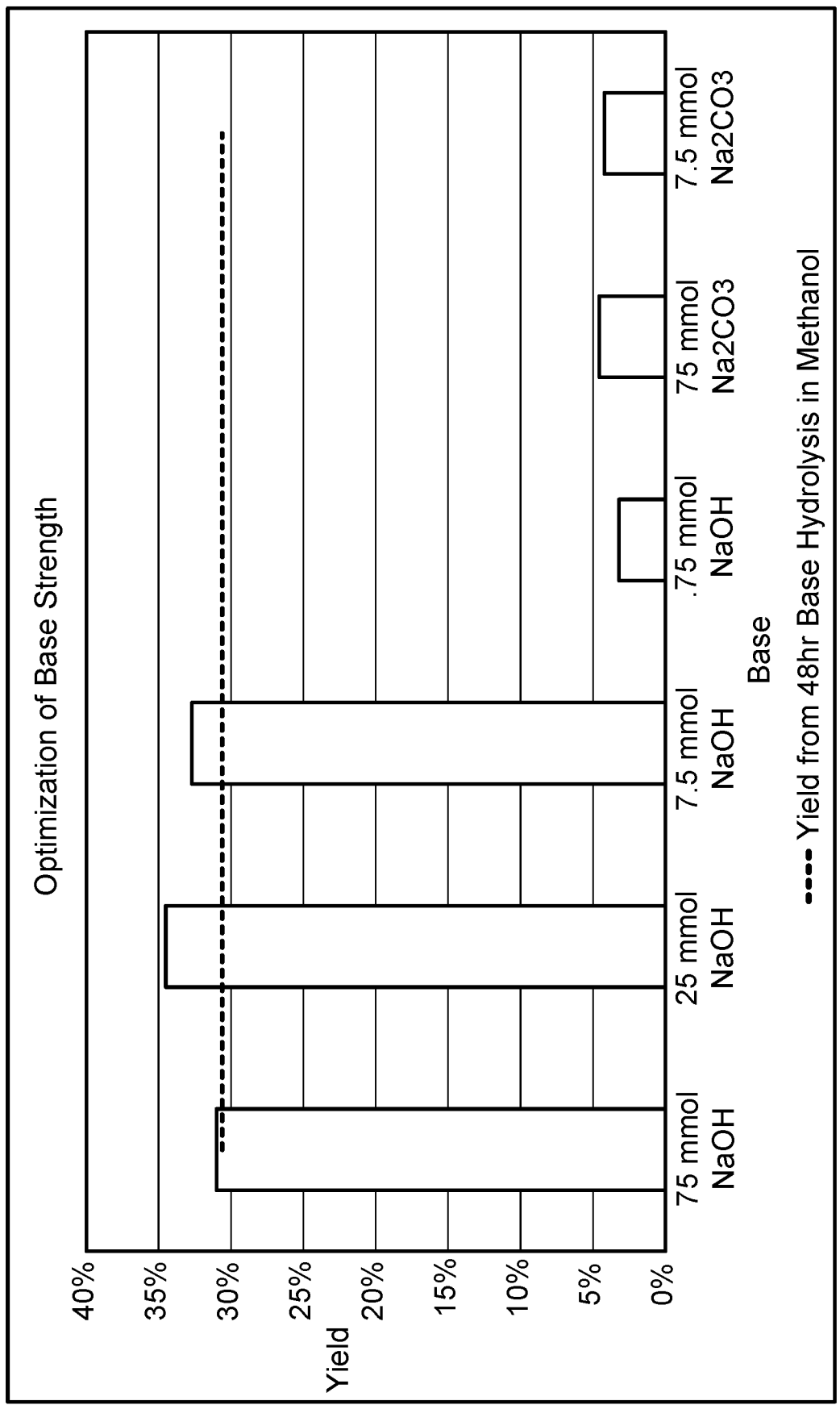
FIG. 2 is graph that shows yield as a function of base for the depolymerization of cutin in a ball mill compared to base hydrolysis in methanol.

The stoichiometry and identity of the base was varied to determine the impact of base strength on the degree of depolymerization and the recovery yield. All experiments were run at 650 rpm in a planetary ball mill for 1 h and employed 1 g of dry tomato peel and 40 g zirconium oxide media. Experiments were run with NaOH loadings of 3 g (75 mmol), 1 g (25 mmol), 0.3 g (7.5 mmol), and 0.03 g (0.75 mmol), or $Na_2CO_3$ at loadings of 8 g (75 mmol), and 0.8 g (7.5 mmol). The results are summarized in Table 3 and plotted in FIG. 2. In general, decreasing base strength in the reaction decreased the contribution from monomer in the product. Optimal results were observed for reactions run with the strong base NaOH at loadings of 3 g, 1 g, and 0.3 g. Lowering the NaOH loading to 0.03 g (Table 3, Entry 4) resulted in a significant drop in monomer contribution and low overall recovery yield. $Na_2CO_3$ was ineffective.

TABLE 3

Effect of base strength on the Depolymerization of Tomato Cutin

| Entry | Base | Base Loading | Recovery (mass recovered/ starting mass) | Product Distribution (GPC) |
|---|---|---|---|---|
| 1 | NaOH | 3 g (75 mmol) | 31% | major monomer, minor dimer and oligomer |
| 2 | NaOH | 1 g (25 mmol) | 35% | major monomer, minor dimer and oligomer |
| 3 | NaOH | 0.3 g (7.5 mmol) | 33% | monomer peak is largest. GPC chromatogram showed slightly more prominent dimer and oligomer peaks. |
| 4 | NaOH | 0.03 g (0.75 mmol) | 3% | GPC chromatogram showed monomer, dimer, and oligomer peaks at roughly the same intensity |
| 5 | $Na_2CO_3$ | 8 g (75 mmol) | 5% | GPC showed a peak for oligomers and a dimer peak that was equal in intensity to the monomer peak |
| 6 | $Na_2CO_3$ | 0.8 g (7.5 mmol) | 4% | GPC chromatogram showed very large oligomer and dimer peaks, and the monomer peak was the smallest |

Example 6. Counter Ion

Figure 3:
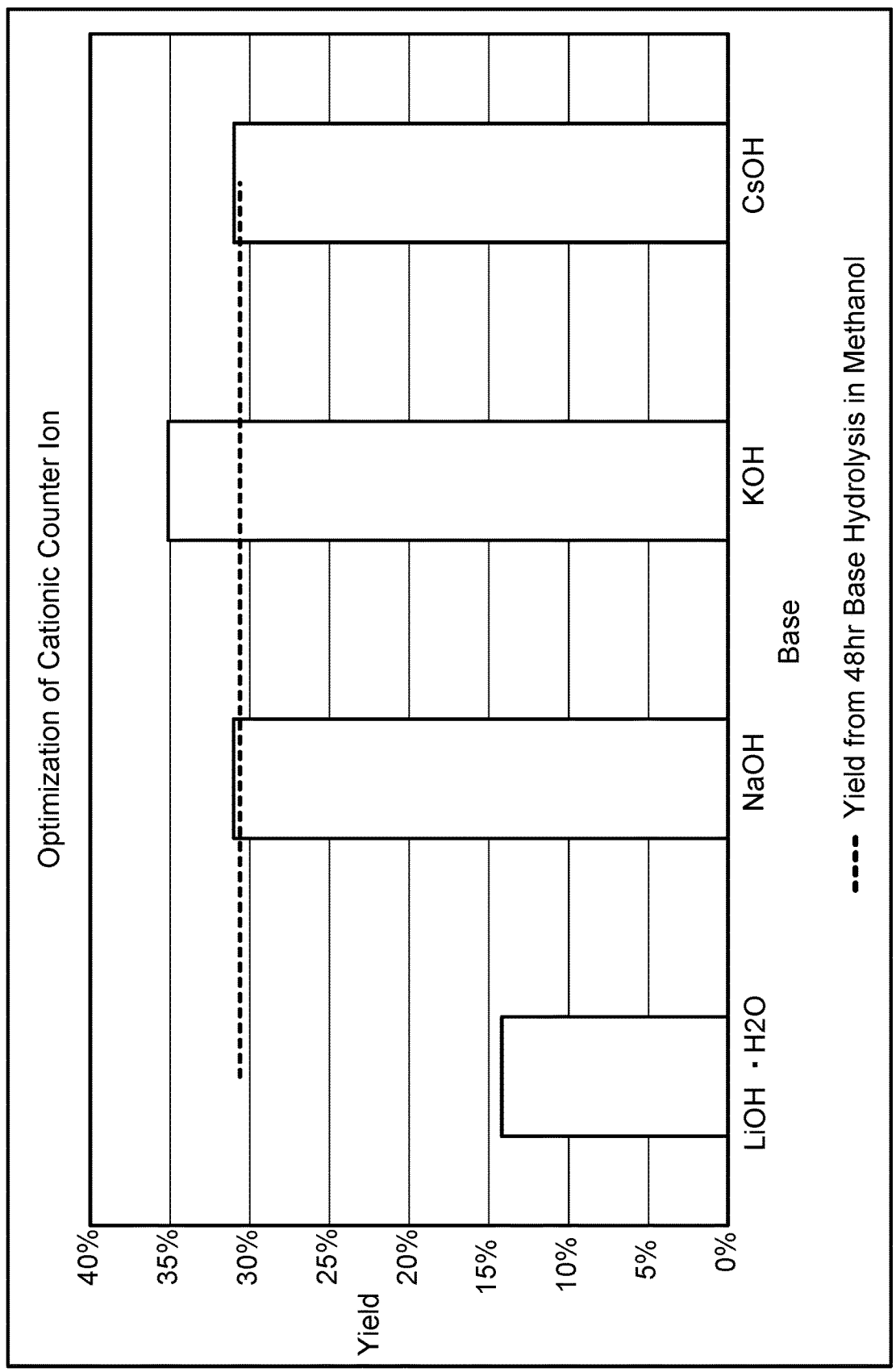
FIG. 3 is a graph that shows yield as a function of counterion for the depolymerization of cutin in a ball mill compared to base hydrolysis in methanol.

The counter ion in the base was varied to determine the impact of the nucleophilicity and size of the cation on the degree of depolymerization and the recovery yield. All experiments were run at 650 rpm in a planetary ball mill for 1 h and employed 1 g of dry tomato peel and 40 g zirconium oxide media. Experiments were run with 75 mmol of the following alkali hydroxides: $LiOH \cdot H_2O$, NaOH, KOH, or $CsOH \cdot H_2O$. The results are summarized in Table 4 and plotted in FIG. 3. The results show that NaOH was the most successful catalyst for the depolymerization of cutin as evidenced by yield and the monomer contribution of the product (Table 4, Entry 2). The experiments with KOH and CsOH resulted in comparable yields to NaOH, however, GPC analysis of the product showed a lower contribution of the monomer, indicating that KOH and CsOH were not as effective as NaOH in fully breaking down the polymer.

TABLE 4

Effect of Counter Ion on the Depolymerization of Tomato Cutin

| Entry | Base | Recovery (mass recovered/ starting mass) | Product Distribution (GPC) |
|---|---|---|---|
| 1 | $LiOH \cdot H_2O$ | 14% | significant dimer, trimer, and oligomer peaks |
| 2 | NaOH | 31% | Major monomer peak, minor dimer and oligomer peaks present |
| 3 | KOH | 35% | significant dimer and oligomer peaks |
| 4 | $CsOH \cdot H_2O$ | 31% | significant dimer and oligomer peaks |

Example 7. Spinning Frequency in the Depolymerization of Tomato Cutin

Figure 4:
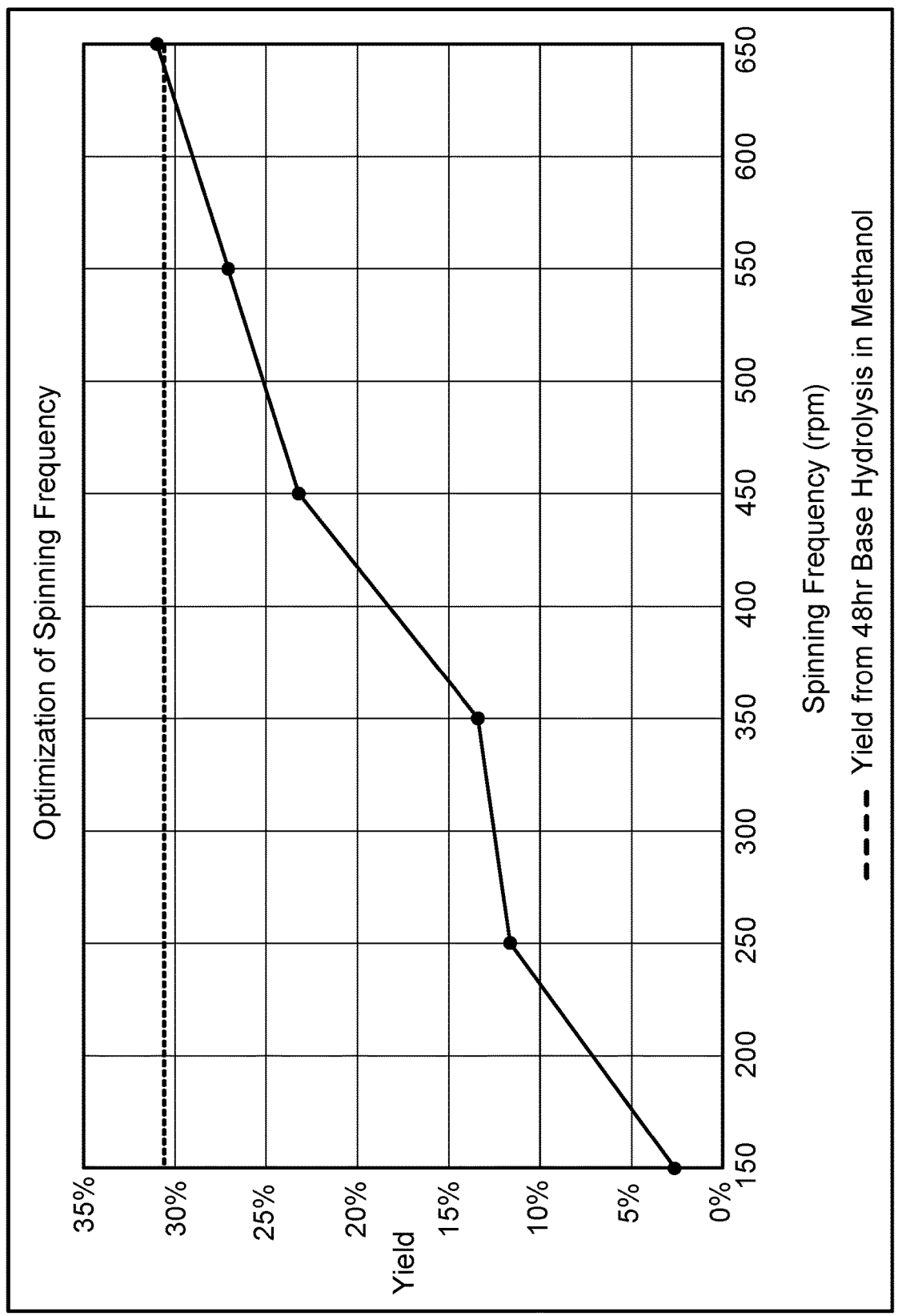
FIG. 4 is a graph that shows yield as a function of spinning frequency for the depolymerization of cutin in a ball mill compared to base hydrolysis in methanol.

The impact that spinning frequency of the ball mill has on the depolymerization of tomato cutin was evaluated. All experiments were run in a Retsch PM 200 planetary ball mill for 1 h, and employed 1 g of dry tomato peel, 40 g zirconium oxide media, and 3 g NaOH. The spinning frequency was investigated in intervals of 100 rpm beginning at 150 rpm and ending at 650 rpm. The results are summarized in Table 5 and plotted in FIG. 4. The results indicate that 650 rpm was the only effective spinning frequency for fully breaking down cutin to its monomer by GPC analysis, in similar yields to experiments performed using traditional chemistry.

TABLE 5

Effect of Spinning Frequency on the Depolymerization of Tomato Cutin

| Entry | Spinning Frequency | Recovery (mass recovered/ starting mass) | Product Distribution (GPC) |
|---|---|---|---|
| 1 | 150 rpm | 3% | significant dimer and oligomer peaks with only slightly less intensity than the monomer peak |
| 2 | 250 rpm | 12% | significant dimer and oligomer peaks with only slightly less intensity than the monomer peak |
| 3 | 350 rpm | 13% | significant dimer and oligomer peaks with only slightly less intensity than the monomer peak |
| 4 | 450 rpm | 23% | large dimer peak with greater intensity than the monomer peak |
| 5 | 550 rpm | 27% | significant dimer peak |
| 6 | 650 rpm | 31% | dimer and oligomer peaks present, but the monomer peak is the largest |

650 rpm was found to be the optimum spinning frequency using a Retsch PM 200 planetary ball mill. However, ball mills having a different configuration may not require as rapid of a spinning frequency or may require a more rapid spinning frequency depending on the energy of impact associated with the grinding process in the ball mill.

Example 8. Effect of Water as an Additive in the Depolymerization of Tomato Cutin The effect of water as an additive in the hydroxide-promoted depolymerization of tomato cutin was evaluated. All experiments were run at 650 rpm in a planetary ball mill for 1 h and employed 1 g of dry tomato peel, 40 g zirconium oxide media, and 3 g NaOH in either the absence or presence of water (1 mL). The results are summarized in Table 6. The reaction run without $H_2O$ led to optimal yield and contribution from monomer in the product by GPC. The addition of water to the reaction only slightly decreased yield, but the monomer contribution dropped significantly in the product of the experiment with added water. The wet experiment still broke the cutin down to the dimer, but the GPC chromatogram showed a notable oligomer peak and very small monomer peak.

TABLE 6

Effect of Water as an Additive on the Depolymerization of Tomato Cutin

| Experiment Number | Water Added | Recovery (mass recovered/ starting mass) | Product Distribution (GPC) |
|---|---|---|---|
| 1 | 0 mL | 31% | major monomer, minor dimer and oligomer |
| 2 | 1 mL | 29% | significant oligomer peaks, and the dimer peak is larger than the monomer peak |

Example 9. Depolymerization of Polyethylene Terephthalate

Mechanochemical depolymerization of polyethylene terephthalate (PET) in a ball mill was performed as follows: PET was shredded in a spice grinder with dry ice, and the shredded PET (1 g, 1 equiv. w/w) was transferred to a grinding jar. NaOH (3 g, 3 equiv. w/w) and 40 g of zirconium oxide media were then added to the grinding jar and the resulting mixture was ground in a planetary ball mill (1 h, 650 rpm).

Workup 1: After completion of the reaction, the ground mixture was diluted with $H_2O$ (150 mL) and filtered. The filtrate was collected and 3M HCl (~30 mL) was added until a solution of pH 3 was obtained. The resulting aqueous solution was extracted with EtOAc (150 mL). The separated EtOAc solution was dried to obtain terephthalic acid monomer (3.81% mass yield) and analyzed by $^1$H NMR.

Workup 2: After completion of the reaction, the ground mixture was diluted with $H_2O$ (100 mL) and filtered. The filtrate was collected and 3M HCl was added until a solution of pH 3 was obtained. The resulting aqueous solution was extracted with EtOAc (2×150 mL), filtered, and the separated EtOAc solution and filter cake were dried to obtain terephthalic acid monomer (6.58% mass yield).

Example 10. Fragmentation of Triglyceride

Hydrogenated grape seed oil (1.00 g, 1.1 mmol) was added to the zirconia milling jar followed by zirconia beads (40 g). Reagent grade, powdered NaOH (0.136 g, 3.4 mmol) was then added to the milling jar, which was capped and milled in the Retsch PM 200 planetary ball mill at 650 rpm for 60 minutes. A small sample was removed from the jar and characterized by IR spectroscopy to confirm the presence of sodium stearate.

Hydrogenated grape seed oil (5.0 g, 5.5 mmol) was added to a 50 mL zirconia milling jar containing 40 g of milling media, and to this was added NaOH (0.68 g, 17 mmol). The ball milling apparatus was then set to 650 rpm for 1 hour. The reaction mixture was passed through a 2 mm sieve to remove the milling media and afforded 5.2 g of hydrogenated grape seed oil fatty acids salts.

Example 11. Fragmentation of Fatty Acid Ester

Ethyl Palmitate (1.00 g, 3.5 mmol) was added to the zirconia milling jar followed by zirconia beads (40 g). Reagent grade, powdered NaOH (0.148 g, 3.7 mmol) was then added to the milling jar, which was capped and milled in the Retsch PM 200 planetary ball mill at 650 rpm for 120 minutes. A small sample was removed from the jar and characterized by IR spectroscopy to confirm the presence of sodium palmitate.

Methyl stearate (1.00 g, 3.4 mmol) was added to the zirconia milling jar followed by zirconia beads (40 g). Reagent grade, powdered NaOH (0.144 g, 3.6 mmol) was then added to the milling jar, which was capped and milled in the Retsch PM 200 planetary ball mill at 650 rpm for 30 minutes. A small sample was removed from the jar and characterized by IR spectroscopy to confirm the presence of sodium stearate.

Example 12. Neutralization of Stearic Acid

Stearic acid (1.00 g, 3.5 mmol) was added to a zirconia milling jar followed by zirconia beads (40 g). Reagent grade, powdered NaOH (0.148 g, 3.7 mmol) was then added to the milling jar, which was capped and milled in the Retsch PM 200 planetary ball mill at 650 rpm for 30 minutes. A small sample was removed from the jar and characterized by IR spectroscopy to confirm the presence of sodium stearate.

Stearic acid (1.00 g, 3.5 mmol) was added to a zirconia milling jar followed by zirconia beads (40 g). Reagent grade, powdered $Na_2CO_3$ (0.148 g, 3.7 mmol) and 0.1 mL water was then added to the milling jar, which was capped and milled in the Retsch PM 200 planetary ball mill at 650 rpm for one hour. The solid was extracted with ethyl acetate to remove any unreacted stearic acid. Analysis of the ethyl acetate showed <1 mg extractable residual stearic acid. A small sample of the ethyl acetate insoluble solid was characterized by IR spectroscopy to confirm the presence of sodium stearate.

A 50 mL zirconia milling jar was charged with stearic acid (1.0 g, 3.5 mmol), powdered NaOH (1.05 equiv), and zirconia milling beads (40 g, 3 mm). The mixture was milled at 650 rpm for 1 hr in a Retsch CM 200 planetary ball mill. The resulting mixture was extracted with hot methanol (50 mL). The solids were removed via filtration over Celite and the filtrate was concentrated under reduced pressure to afford 925 mg of a sodium stearate.

Example 13. Depolymerization of Cutin Using Ultrasonic Energy 31 g of tomato skins (250-500 μm particle size) was mixed with 12.2 g KOH in 300 mL MeOH and sonicated for one hour (applied power was 200 W). After one hour, the solids were filtered off and the methanol evaporated. The crude mass was taken up in 500 mL ethyl acetate and washed 3× in 250 mL water. The ethyl acetate was evaporated to dryness to give 32% of the initial mass recovered as crude, depolymerized DHPA.

Example 14. Direct Access to Fatty Acid Salts from Seeds and Other Biomass

A 50 mL $ZrO_2$ milling jar was charged with ground, dried grape seeds (5 g), powdered NaOH (140 mg), and $ZrO_2$ milling beads (40 g, 3 mm). The mixture was milled at 650 rpm for 1 hr in a Retsch CM 200 planetary ball mill. The resulting mixture was extracted with hot methanol (50 mL). The solids were removed via filtration over Celite and the filtrate was concentrated under reduced pressure to afford 230 mg of a crude mixture of fatty acid salts derived from grape seeds.

A 50 mL $ZrO_2$ milling jar was charged with dried, used coffee grounds (5 g), powdered NaOH (140 mg), and $ZrO_2$ milling beads (40 g, 3 mm). The mixture was milled at 650 rpm for 1 hr in a Retsch CM 200 planetary ball mill. The resulting mixture was extracted with hot methanol (50 mL). The solids were removed via filtration over Celite and the filtrate was concentrated under reduced pressure to afford 150 mg of a crude mixture of fatty acid salts.

What is claimed is:

1. A method for depolymerizing polyester-containing compounds into constituent oligomer and/or monomers, the method comprising:
   contacting a polyester-containing compound with a nucleophile to form a first mixture, wherein the polyester-containing compound is a triglyceride, and the nucleophile is a hydroxide selected from potassium hydroxide, sodium hydroxide, barium hydroxide, cesium hydroxide, and calcium hydroxide;
   mechanically processing the first mixture to decompose at least a portion of the polyester-containing compound to yield a second mixture comprising the constituent oligomer and/or monomers of the polyester-containing compound; and
   isolating at least a portion of the constituent oligomer and/or monomers from the second mixture.

2. The method of claim 1, wherein the mechanical processing comprises grinding the first mixture.

3. The method of claim 2, wherein grinding the first mixture comprises ball milling.

4. The method of claim 2, wherein grinding the first mixture comprises planetary ball milling, and the first mixture is milled at a spinning frequency of about 1 rpm to about 1000 rpm.

5. The method of claim 1, wherein the mechanical processing comprises agitating the first mixture.

6. The method of claim 1, wherein the mechanical processing reduces the particle size of at least a portion of the second mixture to a mean particle size of less than about 1000 microns.

7. The method of claim 1, wherein isolating at least a portion of the constituent monomers from the second mixture comprises treating the second mixture with an acid.

8. The method of claim 7, wherein the acid is an inorganic acid.

9. The method of claim 7, wherein the acid is selected from hydrochloric acid, phosphoric acid, and sulfuric acid.

10. The method of claim 7, wherein treating the second mixture with an acid forms a solution having a pH less than or equal to 5.

11. The method of claim 1, wherein the constituent monomers comprise at least one compound of Formula I:

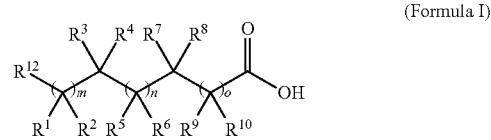

(Formula I)

wherein:
$R^1$, $R^2$, $R^3$, $R^4$, $R^5$, $R^6$, $R^7$, $R^8$, $R^9$, and $R^{10}$ are each independently —H, —$OR^{13}$, —$NR^{13}R^{14}$, —$SR^{13}$, halogen, —$C_1$-$C_6$ alkyl, —$C_2$-$C_6$ alkenyl, —$C_2$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{13}$ and $R^{14}$ are each independently —H, —$C_1$-$C_6$ alkyl, —$C_2$-$C_6$ alkenyl, or —$C_2$-$C_6$ alkynyl, $R^{12}$ is —OH, —H, —$C_1$-$C_6$ alkyl, —$C_2$-$C_6$ alkenyl, —$C_2$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, halogen, —COOH, or —$COOR^{11}$;

m, n, and o are each independently an integer in the range of 0 to 30; and the sum of m, n, and o is 0 to 30.

12. The method of claim 1, wherein the constituent monomers comprise at least one compound of Formula II:

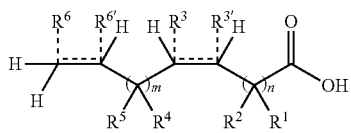

(Formula II)

wherein:

$R^1$, $R^2$, $R^4$, and $R^5$ are each independently —H, —$OR^{11}$, —$NR^{11}R^{12}$, —$SR^{11}$, halogen, —$C_1$-$C_6$ alkyl, —$C_2$-$C_6$ alkenyl, —$C_2$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{11}$, —$NR^{11}R^{12}$, —$SR^{11}$, or halogen;

$R^{11}$ and $R^{12}$ are each independently —H, —$C_1$-$C_6$ alkyl, —$C_2$-$C_6$ alkenyl, or —$C_2$-$C_6$ alkynyl;

the symbol ===== represents an optionally single or cis or trans double bond;

$R^3$ is —OH and $R^{3'}$ is selected from —H, —$C_1$-$C_6$ alkyl, —$C_2$-$C_6$ alkenyl, —$C_2$-$C_6$ alkynyl, —$C_3$-$C_7$ cycloalkyl, and aryl when ===== between $R^3$ and $R^{3'}$ is a single bond, and $R^3$ and $R^{3'}$ are absent when ===== between $R^3$ and $R^{3'}$ represents a double bond;

$R^6$ is —OH and $R^{6'}$ is selected from —H, —$C_1$-$C_6$ alkyl, —$C_2$-$C_6$ alkenyl, —$C_2$-$C_6$ alkynyl, —$C_3$-$C_7$ cycloalkyl, and —$C_6$-$C_{10}$ aryl when ===== between $R^6$ and $R^{6'}$ is a single bond, and $R^6$ and $R^{6'}$ are absent when ===== between $R^6$ and $R^{6'}$ represents a double bond;

n is an integer in the range of 0 to 11;

m is an integer in the range of 0 to 25; and the sum of m and n is 0 to 25.

13. The method of claim 1, wherein the constituent monomers comprise at least one compound of Formula III:

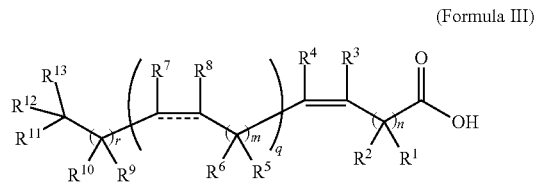

(Formula III)

wherein:

$R^1$, $R^2$, $R^5$, $R^6$, $R^9$, $R^{10}$, $R^{11}$, $R^{12}$, and $R^{13}$ are each independently, at each occurrence, —H, —$OR^{14}$—$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;

$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkenyl, —$C_2$-$C_6$ alkynyl, —$C_3$-$C_7$ cycloalkyl, aryl, or heteroaryl wherein each alkyl, alkynyl, cycloalkyl, aryl, or heteroaryl is optionally substituted with one or more —$OR^{14}$, —$NR^{14}R^{15}$, —$SR^{14}$, or halogen, wherein:

$R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle, and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;

$R^{14}$ and $R^{15}$ are each independently, at each occurrence, —H, —$C_1$-$C_6$ alkyl, —$C_2$-$C_6$ alkenyl, or —$C_2$-$C_6$ alkynyl;

the symbol ===== represents a single bond or a cis or trans double bond;

the symbol ===== represents a cis or trans double bond;

n is 0, 1, 2, 3, 4, 5, 6, 7, or 8;

m is 0, 1, 2, or 3;

q is 0, 1, 2, 3, 4, or 5; and r is 0, 1, 2, 3, 4, 5, 6, 7, or 8.

* * * * *